US012767944B2

(12) United States Patent
Maeda et al.

(10) Patent No.: US 12,767,944 B2
(45) Date of Patent: Oct. 20, 2026

(54) METHOD FOR NONINVASIVELY ACQUIRING MICRO-RNA FROM CELLS

(71) Applicant: NATIONAL INSTITUTE OF ADVANCED INDUSTRIAL SCIENCE AND TECHNOLOGY, Tokyo (JP)

(72) Inventors: Fumio Maeda, Tokyo (JP); Shungo Adachi, Tokyo (JP); Tohru Natsume, Tokyo (JP)

(73) Assignee: National Institute Of Advanced Industrial Science And Technology, Tokyo (JP)

( * ) Notice: Subject to any disclaimer, the term of this patent is extended or adjusted under 35 U.S.C. 154(b) by 465 days.

(21) Appl. No.: 18/576,490

(22) PCT Filed: Jun. 15, 2022

(86) PCT No.: PCT/JP2022/023981
§ 371 (c)(1),
(2) Date: Jan. 4, 2024

(87) PCT Pub. No.: WO2023/281999
PCT Pub. Date: Jan. 12, 2023

(65) Prior Publication Data

US 2024/0318163 A1 Sep. 26, 2024

(30) Foreign Application Priority Data

Jul. 8, 2021 (JP) ................................ 2021-113644

(51) Int. Cl.
*C12N 15/10* (2006.01)
*C12N 5/10* (2006.01)

(52) U.S. Cl.
CPC ..... *C12N 15/1006* (2013.01); *C12N 15/1017* (2013.01)

(58) Field of Classification Search
CPC .. C12N 15/1006; C12N 15/1017; C12N 5/10; C12N 15/10
See application file for complete search history.

(56) References Cited

U.S. PATENT DOCUMENTS

2011/0177054 A1 7/2011 Gibbings et al.
2018/0030429 A1 2/2018 King et al.

FOREIGN PATENT DOCUMENTS

JP 2011524164 A 9/2011
WO WO-2015094609 A1 * 6/2015 ............ G01N 33/53
WO 2016138525 A1 9/2016

OTHER PUBLICATIONS

Easow, George, Aurelio A. Teleman, and Stephen M. Cohen. "Isolation of microRNA targets by miRNP immunopurification." Rna 13.8 (2007): 1198-1204. (Year: 2007).*
Hauptmann, Judith, et al. "Biochemical isolation of Argonaute protein complexes by Ago-APP." Proceedings of the National Academy of Sciences 112.38 (2015): 11841-11845. (Year: 2015).*
Sohel, Mahmodul Hasan. "Extracellular/circulating microRNAs: release mechanisms, functions and challenges." Achievements in the Life Sciences 10.2 (2016): 175-186. (Year: 2016).*
Geekiyanage, Hirosha, et al. "Extracellular microRNAs in human circulation are associated with miRISC complexes that are accessible to anti-AGO2 antibody and can bind target mimic oligonucleotides." Proceedings of the National Academy of Sciences 117.39 (2020): 24213-24223. (Year: 2020).*
"International Search Report and Written Opinion corresponding to International Application No. PCT/2022/023981 mailed Aug. 16, 2022".
Liang, Yuting , et al., "Characterization of protein, long noncoding RNA and micro RNA signatures in extracellular vesicles derived from resting and degranulated mast cells", Journal of Extracellular Vesicles 9:1697583 (Sep. 11, 2019) 20 pages.
Votteler, Jorg , et al., "Designed proteins induce the formation of nanocage-containing extracellular vesicles", Nature 540:292-295 (Dec. 8, 2016).

* cited by examiner

*Primary Examiner* — Abigail Vanhorn
(74) *Attorney, Agent, or Firm* — Myers Bigel, P.A.

(57) ABSTRACT

A method for noninvasively acquiring a microRNA from a cell, the method comprising (1) introducing a nucleic acid coding a microRNA-binding protein and a nucleic acid coding a vesicle-forming protein into the cell, wherein the microRNA-binding protein comprises a first portion consisting of an MID domain and a PIWI domain of an Argonaute protein and a second portion consisting of a virus protein R, and the vesicle-forming protein comprises: a palmitoylation or myristoylation signal or a PH domain; a self-assembling domain; an ESCRT or ESCRT-related factor-binding domain; and a Gag p6 domain; thereby producing an exosome-like vesicle comprising a micro-RNA, (2) collecting an extracellular fluid of the cell, and (3) extracting the micro-RNA from the extracellular fluid.

9 Claims, 9 Drawing Sheets

Specification includes a Sequence Listing.

METHOD FOR NONINVASIVELY ACQUIRING MICRO-RNA FROM CELLS

RELATED APPLICATIONS

This application is a 35 U.S.C. § 371 national phase application of PCT Application PCT/JP2022/023981 filed Jun. 15, 2022, which claims priority to Japanese Application No. 2021-113644 filed Jul. 8, 2021. The entire contents of each are incorporated herein by reference in its entirety.

FIELD OF THE INVENTION

The present invention relates to a method for noninvasively acquiring microRNA from a cell.

BACKGROUND OF THE INVENTION

MicroRNAs (miRNAs) are small, single-stranded non-coding RNAs having a length of about 22 bases, and interact with mRNAs to control expression of the mRNAs. It has been revealed that miRNAs are involved in various biological processes such as cell proliferation, differentiation, apoptosis, and the onset and pathology of various diseases including cancer, and it has been reported that miRNAs have the potential to serve as biomarkers that reflect the state of cells (Non-Patent Document 1). The miRNAs are encapsulated in exosomes secreted from cells and are present in body fluid such as blood or urine, and thus liquid biopsy, which noninvasively diagnoses a disease by detecting and quantifying miRNA in body fluid, is attracting attention. In addition, miRNAs are closely related to the onset and pathology of various diseases, and thus, miRNA-containing exosomes are also anticipated as oligonucleotide therapeutics.

However, miRNA are contained in exosomes only at the concentration in cytoplasm because exosomes are formed by incorporating the cytoplasm. Thus, the amount of miRNAs contained in exosomes is extremely small, and it is difficult to obtain a sufficient amount of miRNAs for accurate diagnosis and drug development.

In recent years, a method for inducing the production of exosome-like extracellular vesicles by using an artificially designed self-assembling protein nanocage has been proposed (Patent Document 1, Non-Patent Document 2). According to this method, exosome-like vesicles that contain a target recombinant protein expressed in the cell can be obtained. However, as well as exosomes, the extracellular vesicles produced this method are also formed by incorporating the cytoplasm, and thus, it is still difficult to acquire miRNAs that are intrinsically present in low abundance in the cytoplasm.

CITATION LIST

Patent Document

[Patent Document 1] WO 2016/138525

Non-Patent Document

[Non-Patent Document 1] Liang, Y. et al., Journal of Extracellular Vesicles, (2019), 9(1):1697583, DOI: 10.1080/20013078.2019.1697583

[Non-Patent Document 2] Votteler, J. et al., Nature, (2016), 540(7632): 292-295, DOI: 10.1038/nature20607

SUMMARY OF INVENTION

Technical Problem

The present invention has been made for the purpose of providing a method for noninvasively acquiring more miRNAs from cells.

Solution to Problem

The inventors have succeeded in increasing the yield of miRNAs by de novo designing a miRNA binding protein having a size at which the protein can be encapsulated in an exosome-like vesicle.

That is, according to one embodiment, the present invention provides a method for noninvasively acquiring a microRNA from a cell, the method comprising: (1) introducing a nucleic acid coding a microRNA-binding protein and a nucleic acid coding a vesicle-forming protein into the cell, wherein the microRNA-binding protein comprises a first portion consisting of an MID domain and a PIWI domain of an Argonaute protein and a second portion consisting of a virus protein R, and wherein the vesicle-forming protein comprises: a palmitoylation or myristoylation signal or a pleckstrin homology domain; a self-assembling domain; an ESCRT or ESCRT-related factor-binding domain; and a Gag p6 domain; thereby an exosome-like vesicle including a microRNA is produced, (2) collecting an extracellular fluid of the cell, and (3) extracting the microRNA from the extracellular fluid.

The microRNA-binding protein preferably comprises an amino acid sequence having at least 90% identity to the amino acid sequence of SEQ ID NO: 1.

The vesicle-forming protein preferably comprises an amino acid sequence having at least 90% identity to an amino acid sequence selected from the group consisting of SEQ ID NOs: 2 to 6.

The cell may be an in vitro cell, and the extracellular fluid may be a culture supernatant.

The cell may be an in vivo cell, and the extracellular fluid may be a biological fluid.

In addition, according to one embodiment, the present invention provides an exosome-like vesicle comprising (a) a microRNA, (b) a microRNA-binding protein comprising a first portion consisting of an MID domain and a PIWI domain of an Argonaute protein and a second portion consisting of a virus protein R, and (c) a nanocage composed of a vesicle-forming protein that comprises an amino acid sequence having at least 90% identity to the amino acid sequence selected from the group consisting of SEQ ID NOs: 2 to 6.

The exosome-like vesicle preferably further comprises (d) a membrane fusion protein.

Advantageous Effects of Invention

According to the method of the present invention, an extracellular fluid that contains miRNAs at a high concentration can be acquired. Thus, the method of the present invention enables noninvasive miRNA analysis, as is conventional miRNA analysis using exosomes, with higher accuracy and sensitivity than such conventional analysis. Also, the exosome-like vesicle according to the present invention contain a high concentration of miRNAs and is useful for the development of nucleic acid medicine.

DESCRIPTION OF EMBODIMENTS

Figure 1:
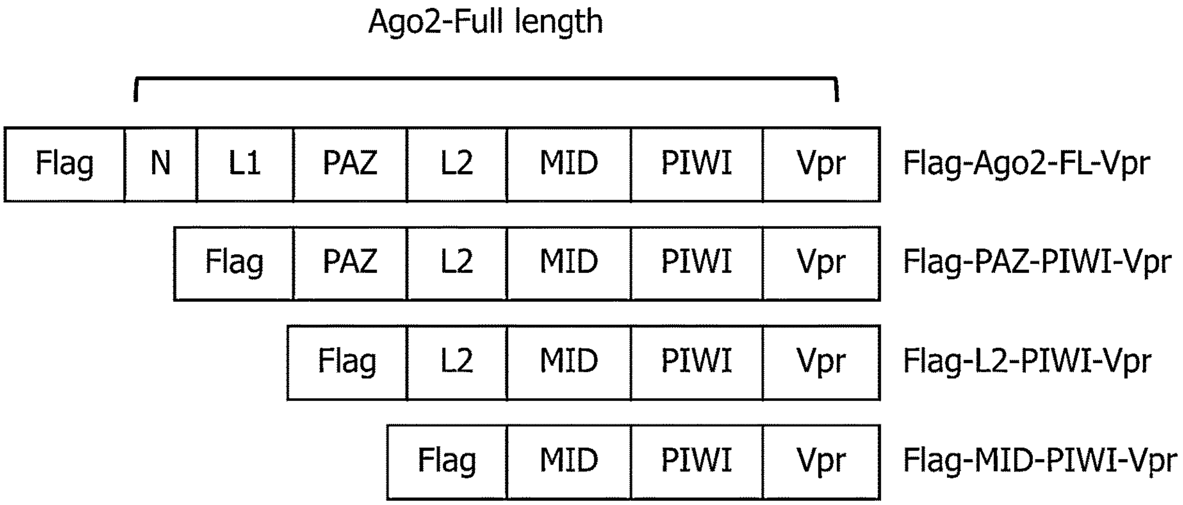
FIG. 1 shows domain structures of various Argonaute protein mutants.

Hereinafter, the present invention will be described in detail, but the present invention is not limited to the embodiments described herein.

According to a first embodiment, the present invention is a method for noninvasively acquiring a microRNA from a cell, the method comprising: (1) introducing a nucleic acid coding a microRNA-binding protein and a nucleic acid coding a vesicle-forming protein into the cell, wherein the microRNA-binding protein comprises a first portion consisting of an MID domain and a PIWI domain of an Argonaute protein and a second portion consisting of a virus protein R, and the vesicle-forming protein comprises: a palmitoylation or myristoylation signal or a pleckstrin homology domain; a self-assembling domain; an ESCRT or ESCRT-related factor-binding domain; and a Gag p6 domain; thereby producing an exosome-like vesicle including a microRNA, (2) collecting an extracellular fluid of the cell, and (3) extracting the microRNA from the extracellular fluid.

In the method of the present embodiment, a nucleic acid coding a microRNA-binding protein and a nucleic acid coding a vesicle-forming protein are introduced into a cell.

A "microRNA" (also referred to as "miRNA") is a small, single-stranded non-coding RNA having a length of about 21 to 25 bases, and more than 20,000 types have been identified thus far (http://mirbase.org/). The miRNA in the present embodiment is not particularly limited, and may be any miRNA expressed in any cell. Also, the miRNA in the present embodiment can be not only a known one but also an unknown one. The miRNA in the present embodiment means a final miRNA product, and does not include intermediate products such as a pri-miRNA or a pre-miRNA.

The type of the "cell" in the present embodiment is not particularly limited, and can be, for example, a dendritic cell, a T cell, a B cell, a neuron, a stem cell, a cancer cell, or a primary culture cell or an established cell line derived therefrom. That is, the cell in the present embodiment may be either an in vivo cell or an in vitro cell. Also, the organism from which the cell is derived is not particularly limited either, and can be any vertebrate, and is preferably a mammal such as a mouse, a rat, a rabbit, a pig, a cow, a goat, a monkey, or a human, and is particularly preferably a human.

The "microRNA-binding protein" in the present embodiment includes a first portion consisting of an MID domain and a PIWI domain of an Argonaute protein and a second portion consisting of a virus protein R.

The "Argonaute protein" (hereinafter also referred to as "Ago") is a protein that binds to a miRNA to form an RNA-induced silencing complex (RISC), and is composed of four characteristic domains: an N domain, a PAZ domain, an MID domain, and a PIWI domain, and two linker domains (L1, L2). The MID domain and the PIWI domain of the Ago used in the present embodiment may be derived from any protein of the Ago family, and are preferably derived from Ago1, Ago2, Ago3, or Ago4, and particularly preferably from Ago2. Also, the MID domain and the PIWI domain of the Ago used in the present embodiment may be derived from any vertebrate, and are preferably from a mammal, and are particularly preferably from a human. The amino acid sequence of human Ago2 (SEQ ID NO: 7) is shown below.

```
MYSGAGPALAPPAPPPPIQGYAFKPPPRPDFGTSGRTIKLQANFFEMDIP

KIDIYHYELDIKPEKCPRRVNREIVEHMVQHEKTQIFGDRKPVFDGRKNL

YTAMPLPIGRDKVELEVTLPGEGKDRIFKVSIKWVSCVSLQALHDALSGR

LPSVPFETIQALDVVMRHLPSMRYTPVGRSFFTASEGCSNPLGGGREVWF

GFHQSVRPSLWKMMLNIDVSATAFYKAQPVIEFVCEVLDFKSIEEQQKPL
```

-continued

TDSQRVKFTKEIKGLKVEITHCGQMKRKYRVCNVTRRPASHQTFPLQQES

GQTVECTVAQYFKDRHKLVLRYPHLPCLQVGQEQKHTYLPLEVCNIVAGQ

RCIKKLTDNQTSTMIRATARSAPDRQEEISKLMRSASFNTDPYVREFGIM

VKDEMTDVTGRVLQPPSILYGGRNKAIATPVQGVWDMRNKQFHTGIEIKV

WAIACFAPQRQCTEVHLKSFTEQLRKISRDAGMPIQGQPCFCKYAQGADS

VEPMFRHLKNTYAGLQLVVVILPGKTPVYAEVKRVGDTVLGMATQCVQMK

NVQRTTPQTLSNLCLKINVKLGGVNNILLPQGRPPVFQQPVIFLGADVTH

PPAGDGKKPSIAAVVGSMDAHPNRYCATVRVQQHRQEIIQDLAAMVRELL

IQFYKSTRFKPTRIIFYRDGVSEGQFQQVLHHELLAIREACIKLEKDYQP

GITFIVVQKRHHTRLFCTDKNERVGKSGNIPAGTTVDTKITHPTEFDFYL

CSHAGIQGTSRPSHYHVLWDDNRFSSDELQILTYQLCHTYVRCTRSVSIP

APAYYAHLVAFRARYHLVDKEHDSAEGSHTSGQSNGRDHQALAKAVQVHQ

DTLRTMYF

The "virus protein R" (hereinafter also referred to as "Vpr") is a type of accessory protein specific to primate immunodeficiency viruses such as human immunodeficiency viruses (HIV) or simian immunodeficiency viruses (SIV), and interacts with the p6 domain of the structural protein Gag of the viruses. The Vpr used in the present embodiment may be derived from any primate immunodeficiency virus, and is preferably derived from an HIV, and particularly preferably from HIV-1. The amino acid sequence of HIV-1 Vpr (SEQ ID NO: 8) is shown below.

MEQAPEDQGPQREPHNEWTLELLEELKREAVRHFPRPWLHGLGQHIYETY

GDTWAGVEAIIRILQQLLFIHFRIGCQHSRIGIIQQRRARRNGASRS

The information of amino acid sequences of Ago and Vpr and nucleic acid sequences coding therefor can be obtained from a predetermined database. For example, for human Ago2, NP_036286.2 (GenBank) and NM_012154.5 (GenBank) are available. For HIV-1 Vpr, NP_057852.2 (GenBank) and NC_001802 (GenBank) (5105 to 5396) are available.

The microRNA-binding protein in the present embodiment most preferably comprises an amino acid sequence consisting of the MID domain and the PIWI domain of human Ago2 and HIV-1-derived Vpr (SEQ ID NO: 1).

MicroRNA-binding protein (SEQ ID NO: 1)

IEIKVWAIACFAPQRQCTEVHLKSFTEQLRKISRDAGMPIQGQPCFCKYA

QGADSVEPMFRHLKNTYAGLQLVVVILPGKTPVYAEVKRVGDTVLGMATQ

CVQMKNVQRTTPQTLSNLCLKINVKLGGVNNILLPQGRPPVFQQPVIFLG

ADVTHPPAGDGKKPSIAAVVGSMDAHPNRYCATVRVQQHRQEIIQDLAAM

VRELLIQFYKSTRFKPTRIIFYRDGVSEGQFQQVLHHELLAIREACIKLE

KDYQPGITFIVVQKRHHTRLFCTDKNERVGKSGNIPAGTTVDTKITHPTE

FDFYLCSHAGIQGTSRPSHYHVLWDDNRFSSDELQILTYQLCHTYVRCTR

SVSIPAPAYYAHLVAFRARYHLVDKEHDSAEGSHTSGQSNGRDHQALAKA

-continued

VQVHQDTLRTMYFASRLEDIGGGGGGEQAPEDQGPQREPHNEWTLELLEE

LKREAVRHFPRPWLHGLGQHIYETYGDTWAGVEAIIRILQQLLFIHFRIG

CQHSRIGIIQQRRARRNGASRS

The microRNA-binding protein in the present embodiment may include a protein consisting of an amino acid sequence having an identity of 80% or more, preferably 90% or more, more preferably about 95% or more with the above amino acid sequences registered in the database, as long as binding activity to miRNA equivalent to the MID and PIWI domains of Ago and to the p6 domain of Gag equivalent to Vpr is maintained. The amino acid sequence identity can be determined by using sequence analysis software or by using a program commonly used in the art (FASTA, BLAST, etc.).

The "vesicle-forming protein" in the present embodiment includes a palmitoylation or myristoylation signal or a pleckstrin homology (PH) domain, a self-assembling domain, an ESCRT or ESCRT-related factor-binding domain, and a Gag p6 domain. A vesicle-forming protein that can be used in the present embodiment is disclosed, for example, as Enveloped Protein Nanocage (EPN) in WO 2016/138525, and specific examples thereof include, but are not limited to, EPN-01 (SEQ ID NO: 2), EPN-03 (SEQ ID NO: 3), EPN-07 (SEQ ID NO: 4), EPN-08 (SEQ ID NO: 5), and EPN-18 (SEQ ID NO: 6). The vesicle-forming protein in the present embodiment is preferably EPN-01 (SEQ ID NO: 2).

EPN-01

(SEQ ID NO: 2)

MGARASGSKSGSGSDSGSKIEELFKKHKIVAVLRANSVEEAKKKALAVFL

GGVHLIEITFTVPDADTVIKELSFLKEMGAIIGAGTVTSVEQCRKAVESG

AEFIVSPHLDEEISQFCKEKGVFYMPGVMTPTELVKAMKLGHTILKLFPG

EVVGPQFVKAMKGPFPNVKFVPTGGVNLDNVCEWFKAGVLAVGVGSALVK

GTPVEVAEKAKAFVEKIRGCTEQKLISEEDLQSRPEPTAPPEESFRSGVE

TTTPPQKQEPIDKELYPLTSLRSLFGNDPSSQ

EPN-03

(SEQ ID NO: 3)

MGAQFSGSKSGSGSDSGSKIEELFKKHKIVAVLRANSVEEAKKKALAVFL

GGVHLIEITFTVPDADTVIKELSFLKEMGAIIGAGTVTSVEQCRKAVESG

AEFIVSPHLDEEISQFCKEKGVFYMPGVMTPTELVKAMKLGHTILKLFPG

EVVGPQFVKAMKGPFPNVKFVPTGGVNLDNVCEWFKAGVLAVGVGSALVK

GTPVEVAEKAKAFVEKIRGCTEQKLISEEDLQSRPEPTAPPEESFRSGVE

TTTPPQKQEPIDKELYPLTSLRSLFGNDPSS

EPN-07

(SEQ ID NO: 4)

MGCIKSKRKDNLNGSKSGSGSDSGSKIEELFKKHKIVAVLRANSVEEAKK

KALAVFLGGVHLIEITFTVPDADTVIKELSFLKEMGAIIGAGTVTSVEQC

RKAVESGAEFIVSPHLDEEISQFCKEKGVFYMPGVMTPTELVKAMKLGHT

ILKLFPGEVVGPQFVKAMKGPFPNVKFVPTGGVNLDNVCEWFKAGVLAVG

VGSALVKGTPVEVAEKAKAFVEKIRGCTEQKLISEEDLQSRPEPTAPPEE

SFRSGVETTTPPQKQEPIDKELYPLTSLRSLEGNDPSS

-continued

EPN-08

(SEQ ID NO: 5)

```
MGCTLSAEERAALGSKSGSGSDSGSKIEELFKKHKIVAVLRANSVEEAKK

KALAVFLGGVHLIEITFTVPDADTVIKELSFLKEMGAIIGAGTVTSVEQC

RKAVESGAEFIVSPHLDEEISQFCKEKGVFYMPGVMTPTELVKAMKLGHT

ILKLFPGEVVGPQFVKAMKGPFPNVKFVPTGGVNLDNVCEWFKAGVLAVG

VGSALVKGTPVEVAEKAKAFVEKIRGCTEQKLISEEDLQSRPEPTAPPEE

SFRSGVETTTPPQKQEPIDKELYPLTSLRSLF
```

EPN-18

(SEQ ID NO: 6)

```
MHGLQDDPDLQALLKGSQLLKVKSSSWRRERFYKLQEDCKTIWQESRKVM

RSPESQLFSIEDIQEVRMGHRTEGLEKFARDIPEDRCFSIVFKDQRNTLD

LIAPSPADAQHWVQGLRKIIHHSGSMDQRQKGSGSKIEELFKKHKIVAVL

RANSVEEAKKKALAVFLGGVHLIEITFTVPDADTVIKELSFLKEMGAIIG

AGTVTSVEQCRKAVESGAEFIVSPHLDEEISQFCKEKGVFYMPGVMTPTE

LVKAMKLGHTILKLFPGEVVGPQFVKAMKGPFPNVKFVPTGGVNLDNVCE

WFKAGVLAVGVGSALVKGTPVEVAEKAKAFVEKIRGCTEQKLISEEDLQS

RPEPTAPPEESFRSGVETTTPPQKQEPIDKELYPLTSLRSLFGNDPSSQ
```

The vesicle-forming protein in the present embodiment can include a protein consisting of an amino acid sequence having an identity of 80% or more, preferably 90% or more, more preferably about 95% or more with the above amino acid sequences of the EPN subunits disclosed in the above publication, as long as activities of the EPN subunits are maintained (that is, nanocages can be formed by self-assembly to constitute extracellular vesicles).

The microRNA-binding protein and the vesicle-forming protein in the present embodiment may comprise an epitope tag, such as Myc, HA, or FLAG, added to the N-terminus and/or the C-terminus thereof.

A nucleic acid coding the microRNA-binding protein and a nucleic acid coding the vesicle-forming protein can be prepared by any conventionally known genetic engineering method using the sequences designed according to the above. Also, these nucleic acids may be introduced into a cell by well-known methods in the art, e.g., the nucleic acids may be cloned into an expression vector and thereby introduced into a cell. The type of the expression vector is not particularly limited, and the expression vector may be either a virus vector or a non-virus vector, and may be, e.g., a virus vector such as a herpesvirus vector, an adenovirus vector, a lentivirus vector, or a retrovirus vector, or a plasmid vector such as pCMV or pCAG.

When the microRNA-binding protein and the vesicle-forming protein are expressed in cells, microRNA-binding protein-miRNA complexes are stored in nanocages composed of the vesicle-forming proteins, and an exosome-like vesicles are formed and released outside the cell. The "exosome-like vesicle" in the present embodiment refers to nanoscale extracellular vesicles that are similar in structure and composition to exosomes.

Next, an extracellular fluid of the cell is collected. If the cell is an in vitro cell, the extracellular fluid may be a culture supernatant, and if the cell is an in vivo cell, the extracellular fluid may be a biological fluid. Examples of the biological fluid include, but are not limited to, blood, plasma, serum, saliva, and urine.

Next, miRNA is extracted from the extracellular fluid. The miRNA can be extracted by any established procedures, e.g., extracellular vesicles can be collected by ultracentrifugation and miRNAs can be isolated by purification methods such as the Boom method. Numerous miRNA extraction kits based on the Boom method are commercially available, and such commercially available products can also be used in the method of the present embodiment. Examples of a preferable commercially available products include High Pure miRNA Isolation Kit (Roche Diagnostics), miRNeasy Mini Kit (Qiagen), and mirVana™ miRNA Isolation Kit (Thermo Fisher Scientific).

The method of the present embodiment can acquire extracellular fluid containing high concentrations of miRNAs, enabling noninvasive, highly accurate, and highly sensitive diagnosis.

According to a second embodiment, the present invention is an exosome-like vesicle comprising (a) a microRNA, (b) a microRNA-binding protein comprising a first portion consisting of an MID domain and a PIWI domain of an Argonaute protein and a second portion consisting of a virus protein R, and (c) a nanocage composed of a vesicle-forming protein comprising an amino acid sequence having at least 90% identity to an amino acid sequence selected from the group consisting of SEQ ID NOs: 2 to 6.

The "exosome-like vesicle," "microRNA," "Argonaute protein," "viral protein R," "microRNA-binding protein," and "vesicle-forming protein" in the present embodiment are as defined in the first embodiment.

The exosome-like vesicle of the present embodiment can further comprise (d) a membrane fusion protein. The "membrane fusion protein" means a protein that causes fusion between homogeneous or heterologous cells or membrane vesicles. The membrane fusion protein in the present embodiment is not particularly limited, and it is preferably an enveloped virus-derived membrane fusion protein, and examples thereof include vesicular stomatitis virus G protein (VSV-G), herpes simplex virus glycoprotein B (gB), and a recombinant thereof.

The exosome-like vesicle of the present embodiment can be acquired from extracellular fluid of cells into which a nucleic acid coding a microRNA-binding protein and a nucleic acid coding a vesicle-forming protein are introduced by the procedure of the method of the first embodiment.

The exosome-like vesicle of the present embodiment can contain a miRNA at a higher concentration than a natural exosome. Because of this, the exosome-like vesicle of the present embodiment is useful for diagnosis of a disease and development of a nucleic acid drug.

EXAMPLES

The present invention will be further described with reference to Examples shown below. These by no means limit the present invention.

1. Search for Argonaute Protein Mutants that can be Stored in Extracellular Vesicles In the present Example, EPN-01 (SEQ ID NO: 2) was used as the vesicle-forming protein, and human Ago2 was used as the Argonaute protein. Since the nanocage formed by EPN-01 was 20 nm in diameter, it was assumed that it would be difficult for the full-length Ago2 to be encapsulated therein. Thus, mutants having different sizes were prepared from Ago2, and they were tested to see if these could be encapsulated in the nanocage.

Expression vectors for Ago2 mutants of the full-length Ago2 (amino acids 1 to 860), the PAZ domain to the PIWI domain of Ago2 (amino acids 227 to 860), the L2 domain to the PIWI domain of Ago2 (amino acids 347 to 860), and the MID domain to the PIWI domain of Ago2 (amino acids 446 to 860), with a FLAG tag added to the N-terminus and HIV-1-derived Vpr (SEQ ID NO: 1) added to the C-terminus (Flag-Ago2-FL-Vpr, Flag-PAZ-PIWI-Vpr, Flag-L2-PIWI-Vpr, and Flag-MID-PIWI-Vpr, respectively, FIG. 1), were prepared by the following procedures.

We commissioned VectorBuilder, Inc., to synthesize a plasmid VB200705-1156knk (SEQ ID NO: 9), comprising sequences coding EPN-01 and Myc-EGFP-Vpr. Inverse PCR was performed using VB200705-1156knk as a template with the following primers 1 and 2. The resulting amplified product was cleaved at the EcoRI site and ligated to obtain pRP-Myc-EGFP-Vpr. PCR was performed using pcDNA3.2-5'F-Ago2, a plasmid comprising a sequence coding full-length human Ago2 with a Flag tag added to the N-terminus, as a template with the following primers 3 and 4. The resulting amplification product was inserted into the XbaI site of pRP-Myc-EGFP-Vpr by In-Fusion cloning to obtain pRP-Flag-Ago2-FL-Vpr, a plasmid comprising a sequence coding Flag-Ago2-FL-Vpr. PCR was performed using pRP-Flag-Ago2-FL-Vpr as a template with the following primers 5 and 6. The resulting amplified product was inserted into the NheI/HindIII site of pEGFP-C2 (Clontech) by In-Fusion cloning to obtain pCMV-Flag-Ago2-FL-Vpr.

PCR was performed using pcDNA3.2-5'F-Ago2 as a template with the following primers 7 and 10, 8 and 10, or 9 and 10. The resulting amplified product was inserted into the NheI/XbaI site of pCMV-Flag-Ago2-FL-Vpr by In-Fusion cloning to obtain pCMV-Flag-PAZ-PIWI-Vpr, pCMV-Flag-L2-PIWI-Vpr, and pCMV-Flag-MID-PIWI-Vpr.

TABLE 1

Primer sets for constructing Ago2 mutant expression vectors [Table 1]

| No. | Primer name | Sequence (5'→3') | SEQ ID NO |
|---|---|---|---|
| 1 | EcoR1-Myc-EGFP_F | GCGAATTCTTAATTAATCTAGACATGGA | 10 |
| 2 | EF1A-EcoR1_R | GCGAATTCAGCCTGCTTTTTTGTACAAA | 11 |
| 3 | VLP-Flag-Ago2_F | TTAATTAATCTAGACATGGATTACAAAGACGATGACGATAAGATGTACTCGGGAGCCGGCCC | 12 |
| 4 | VLP-Ago2_R | ATCCTCGAGTCTAGAAGCAAAGTACATGGTGCGCA | 13 |
| 5 | pΔEGFP_Flag_F | GTCAGATCCGCTAGCGCCACCATGGATTACAAAGACGATGA | 14 |
| 6 | PRP_pΔEGFP-C2_R | CAGAATTCGAAGCTTTTTGTACAAGAAAGCTGGGT | 15 |
| 7 | pdEGFP_Flag-Ago2_Paz-PIWI_F | GTCAGATCCGCTAGCGCCACCATGGATTACAAAGACGATGACGATGCACAGCCAGTAATCGAGTT | 16 |
| 8 | pdEGFP_Flag-Ago2_L2-PIWI_F | GTCAGATCCGCTAGCGCCACCATGGATTACAAAGACGATGACGATGCAGGACAAAGATGTATTAA | 17 |
| 9 | pdEGFP_Flag-Ago2-dN-PAZ_F | GTCAGATCCGCTAGCGCCACCATGGATTACAAAGACGATGACGATAAGATCGAGATCAAGGTGTGGGC | 18 |

TABLE 1-continued

Primer sets for constructing Ago2 mutant expression vectors [Table 1]

| No. | Primer name | Sequence (5'→3') | SEQ ID NO |
|---|---|---|---|
| 10 | Ago2-Xba-Vpr_R | TCCGATATCCTCGAGAGCAAAGTACATGGTGCGCA | 19 |

The amino acid sequences of Flag-Argonaute protein mutant-Vpr expressed from the plasmid vectors prepared above are shown below.

Flag-Ago2-FL-Vpr (SEQ ID NO: 23)

MDYKDDDDKMYSGAGPALAPPAPPPPIQGYAFKPPPRPDFGTSGRTIKLQ
ANFFEMDIPKIDIYHYELDIKPEKCPRRVNREIVEHMVQHFKTQIFGDRK
PVFDGRKNLYTAMPLPIGRDKVELEVTLPGEGKDRIFKVSIKWVSCVSLQ
ALHDALSGRLPSVPFETIQALDVVMRHLPSMRYTPVGRSFFTASEGCSNP
LGGGREVWFGFHQSVRPSLWKMMLNIDVSATAFYKAQPVIEFVCEVLDFK
SIEEQQKPLTDSQRVKFTKEIKGLKVEITHCGQMKRKYRVCNVTRRPASH
QTFPLQQESGQTVECTVAQYFKDRHKLVLRYPHLPCLQVGQEQKHTYLPL
EVCNIVAGQRCIKKLTDNQTSTMIRATARSAPDRQEEISKLMRSASFNTD
PYVREFGIMVKDEMTDVTGRVLQPPSILYGGRNKAIATPVQGVWDMRNKQ
FHTGIEIKVWAIACFAPQRQCTEVHLKSFTEQLRKISRDAGMPIQGQPCF
CKYAQGADSVEPMFRHLKNTYAGLQLVVVILPGKTPVYAEVKRVGDTVLG
MATQCVQMKNVQRTTPQTLSNLCLKINVKLGGVNNILLPQGRPPVFQQPV
IFLGADVTHPPAGDGKKPSIAAVVGSMDAHPNRYCATVRVQQHRQEIIQD
LAAMVRELLIQFYKSTRFKPTRIIFYRDGVSEGQFQQVLHHELLAIREAC
IKLEKDYQPGITFIVVQKRHHTRLFCTDKNERVGKSGNIPAGTTVDTKIT
HPTEFDFYLCSHAGIQGTSRPSHYHVLWDDNRFSSDELQILTYQLCHTYV
RCTRSVSIPAPAYYAHLVAFRARYHLVDKEHDSAEGSHTSGQSNGRDHQA
LAKAVQVHQDTLRTMYFASRLEDIGGGGGGEQAPEDQGPQREPHNEWTLE
LLEELKREAVRHFPRPWLHGLGQHIYETYGDTWAGVEAIIRILQQLLFIH
FRIGCQHSRIGIIQQRRARRNGASRS

Flag-PAZ-PIWI-Vpr (SEQ ID NO: 24)

MDYKDDDDKAQPVIEFVCEVLDFKSIEEQQKPLTDSQRVKFTKEIKGLKV
EITHCGQMKRKYRVCNVTRRPASHQTFPLQQESGQTVECTVAQYFKDRHK
LVLRYPHLPCLQVGQEQKHTYLPLEVCNIVAGQRCIKKLTDNQTSTMIRA
TARSAPDRQEEISKLMRSASENTDPYVREFGIMVKDEMTDVTGRVLQPPS
ILYGGRNKAIATPVQGVWDMRNKQFHTGIEIKVWAIACFAPQRQCTEVHL
KSFTEQLRKISRDAGMPIQGQPCFCKYAQGADSVEPMFRHLKNTYAGLQL
VVVILPGKTPVYAEVKRVGDTVLGMATQCVQMKNVQRTTPQTLSNLCLKI
NVKLGGVNNILLPQGRPPVFQQPVIFLGADVTHPPAGDGKKPSIAAVVGS
MDAHPNRYCATVRVQQHRQEIIQDLAAMVRELLIQFYKSTREKPTRIIFY

-continued

```
RDGVSEGQFQQVLHHELLAIREACIKLEKDYQPGITFIVVQKRHHTRLFC
TDKNERVGKSGNIPAGTTVDTKITHPTEFDFYLCSHAGIQGTSRPSHYHV
LWDDNRESSDELQILTYQLCHTYVRCTRSVSIPAPAYYAHLVAFRARYHL
VDKEHDSAEGSHTSGQSNGRDHQALAKAVQVHQDTLRTMYFASRLEDIGG
GGGGEQAPEDQGPQREPHNEWTLELLEELKREAVRHFPRPWLHGLGQHIY
ETYGDTWAGVEAIIRILQQLLFIHFRIGCQHSRIGIIQQRRARRNGASRS
```

Flag-L2-PIWI-Vpr (SEQ ID NO: 25)

```
MDYKDDDDKAGQRCIKKLTDNQTSTMIRATARSAPDRQEEISKLMRSASF
NTDPYVREFGIMVKDEMTDVTGRVLQPPSILYGGRNKAIATPVQGVWDMR
NKQFHTGIEIKVWAIACFAPQRQCTEVHLKSFTEQLRKISRDAGMPIQGQ
PCFCKYAQGADSVEPMFRHLKNTYAGLQLVVVILPGKTPVYAEVKRVGDT
VLGMATQCVQMKNVQRTTPQTLSNLCLKINVKLGGVNNILLPQGRPPVFQ
QPVIFLGADVTHPPAGDGKKPSIAAVVGSMDAHPNRYCATVRVQQHRQEI
IQDLAAMVRELLIQFYKSTRFKPTRIIFYRDGVSEGQFQQVLHHELLAIR
EACIKLEKDYQPGITFIVVQKRHHTRLFCTDKNERVGKSGNIPAGTTVDT
KITHPTEFDFYLCSHAGIQGTSRPSHYHVLWDDNRFSSDELQILTYQLCH
TYVRCTRSVSIPAPAYYAHLVAFRARYHLVDKEHDSAEGSHTSGQSNGRD
HQALAKAVQVHQDTLRTMYFASRLEDIGGGGGGEQAPEDQGPQREPHNEW
TLELLEELKREAVRHFPRPWLHGLGQHIYETYGDTWAGVEAIIRILQQLL
FIHFRIGCQHSRIGIIQQRRARRNGASRS
```

Flag-MID-PIWI-Vpr (SEQ ID NO: 26)

```
MDYKDDDDKIEIKVWAIACFAPQRQCTEVHLKSFTEQLRKISRDAGMPIQ
GQPCFCKYAQGADSVEPMFRHLKNTYAGLQLVVVILPGKTPVYAEVKRVG
DTVLGMATQCVQMKNVQRTTPQTLSNLCLKINVKLGGVNNILLPQGRPPV
FQQPVIFLGADVTHPPAGDGKKPSIAAVVGSMDAHPNRYCATVRVQQHRQ
EIIQDLAAMVRELLIQFYKSTREKPTRIIFYRDGVSEGQFQQVLHHELLA
IREACIKLEKDYQPGITFIVVQKRHHTRLFCTDKNERVGKSGNIPAGTTV
DTKITHPTEFDFYLCSHAGIQGTSRPSHYHVLWDDNRESSDELQILTYQL
CHTYVRCTRSVSIPAPAYYAHLVAFRARYHLVDKEHDSAEGSHTSGQSNG
RDHQALAKAVQVHQDTLRTMYFASRLEDIGGGGGGEQAPEDQGPQREPHN
EWTLELLEELKREAVRHFPRPWLHGLGQHIYETYGDTWAGVEAIIRILQQ
LLFIHFRIGCQHSRIGIIQQRRARRNGASRS
```

PCR was performed using VB200705-1156knk (SEQ ID NO: 9) as a template with the following primers 11 and 12, so as to construct an EPN-01 expression vector. The resulting amplified product was cleaved at the KpnI site and ligated to obtain pRP-EPN-01. PCR was performed using pRP-EPN-01 as a template with the primer 6 above and primer 13 below. The resulting amplified product was inserted into the NheI/HindIII site of pEGFP-C2 by In-Fusion cloning to obtain pCMV-EPN-01.

TABLE 2

Primer sets for constructing Ago2 mutant expression vectors [Table 2]

| No. | Primer name | Sequence (5'→3') | SEQ ID NO |
|---|---|---|---|
| 11 | kpn1-SV40_F | GCGGTACCACCCAGCTTTCTTGTACAAA | 20 |
| 12 | EPN01-kpn1_R | GCGGTACCTTACTGAGAAGACGGGTCGTTAC | 21 |
| 13 | pΔEGFP_EPN01_F | GTCAGATCCGCTAGCGCCACCATGGGTGCGCGTGC | 22 |

HEK293T cells (ATCC) were placed in a 10 cm dish. The next day, each Ago2 mutant expression vector (5 μg) and the EPN-01 expression vector (10 μg) were transfected with Lipofectamine 2000 (Thermo Fisher Scientific), and after 6 hours, the medium was replaced with 10 ml of fresh medium. At 24 hours after transfection, the medium was collected and centrifuged at 200×g for 5 minutes at 4° C., at 1,000×g for 5 minutes at 4° C., and at 10,000×g for 30 minutes at 4° C. to collect the supernatant. The supernatant was layered on 2 ml of a 20% sucrose solution placed in an ultracentrifugation tube, and ultracentrifuged at 100,000×g for 90 minutes at 4° C. After that, the supernatant was discarded, and the pellet was gently washed with PBS. The liquid was removed, and then 100 μl of 1×SDS sample buffer (Tris-HCl (62.5 mM), pH 6.8, 20% glycerol, 2% SDS, 2.5% 2-mercaptoethanol) was added to the bottom without touching the wall of the tube to dissolve the pellet to obtain an extracellular-vesicle solution. The obtained solution was stored at −80° C. On the other hand, the HEK293T cells after collection of the medium were washed with PBS, collected, and ⅕ amount thereof was dissolved in 200 μl of 1× SDS sample buffer to obtain a cell solution.

The extracellular-vesicle solution and the cell solution were subjected to SDS-PAGE (10% acrylamide gel), and after electrophoresis, proteins were transferred to a PDVF membrane. After the transfer, the PDVF membrane was blocked with 3.5% skim milk for 30 minutes, washed with TBS-T (Tris-HCl (25 mM), NaCl (150 mM), 0.1% Tween 20) three times (30 minutes in total), and then incubated in a primary antibody solution overnight at 4° C. The primary antibody solution was removed, the PDVF membrane was washed with TBS-T three times (30 minutes in total), and then incubated in a secondary antibody solution for 1 hour at room temperature. The secondary antibody solution was removed, and the PDVF membrane was washed with TBS-T three times (30 minutes in total), and then a reaction for detection using ImmunoStar LD (Wako) was carried out, which was detected with LAS3000 (FUJIFILM). As the primary antibody, an anti-c-Myc antibody (anti-c-myc from mouse IgGIK [9E10] (11667203001, Roche) (1:1000 dilution)); an anti-Flag antibody (Monoclonal ANTI-FLAG™ M2 antibody produced in mouse (F3165, Sigma-Aldrich (1:1000 dilution)); and an anti-ß-actin antibody (B-Actin (13E5) Rabbit mAb (#4970, Cell Signaling Technology) (1:1000 dilution)) were used. As the secondary antibody, ECL™ anti-rabbit IgG (NA9340V, GE) (1:2000 dilution) and ECL™ anti-mouse IgG (NA9310V, GE) (1:2000 dilution) were used.

Figure 2:
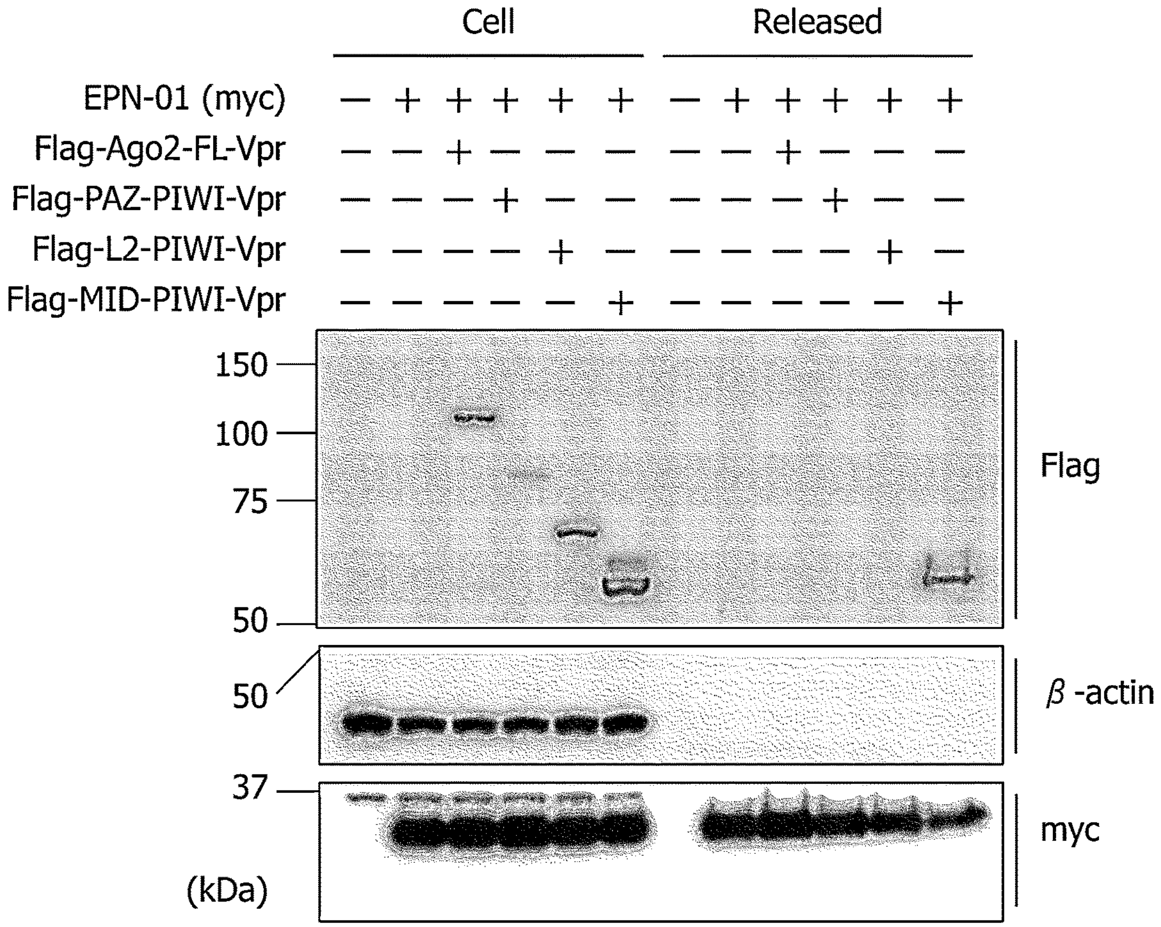
FIG. 2 shows results of Western blot analysis confirming various Argonaute protein mutants in cells and in extracellular vesicles.

Results are shown in FIG. 2. Hereinafter, in the Figure, “Cell” indicates the results for the cell solution, and "Released" indicates the results for the extracellular-vesicle solution. Expression of the full-length Ago2 and all the Ago2 mutants was observed in the cell solution, but only the MID-PIWI-Vpr mutant was detected in the extracellular-vesicle solution. These results confirm that only the MID-PIWI-Vpr mutant can be incorporated into an EPN-01 nanocage.

2. miRNA Binding Activity of MID-PIWI-Vpr Mutant

Next, in order to examine the miRNA-binding activity of the MID-PIWI-Vpr mutant, the full-length Ago2 (Flag-Ago2-FL-Vpr) or Flag-MID-PIWI-Vpr was expressed in HEK293T cells by the same procedure as in 1 above. As a control, EGFP was expressed instead of the Ago2 mutant. At 24 hours after transfection, the cells were washed once with PBS, and 1 mL of Lysis Buffer (HEPES (20 mM), pH 7.5, NaCl (150 mM), NaF (50 mM), $Na_3$ $VO_4$ (1 mM), 1% Digitonin, phenylmethylsulfonyl fluoride (1 mM), Leupeptin (5 μg/ml), Aprotinin (5 μg/ml), Pepstatin A (3 μg/ml)) was added. The cell lysate was collected with a scraper and centrifuged at 15,000 rpm for 10 minutes at 4° C., and the supernatant was collected. A 50 μl aliquot was taken from the supernatant, and 50 μl of 2× SDS sample buffer was added thereto to obtain a cell solution sample before immunoprecipitation.

Figure 3:
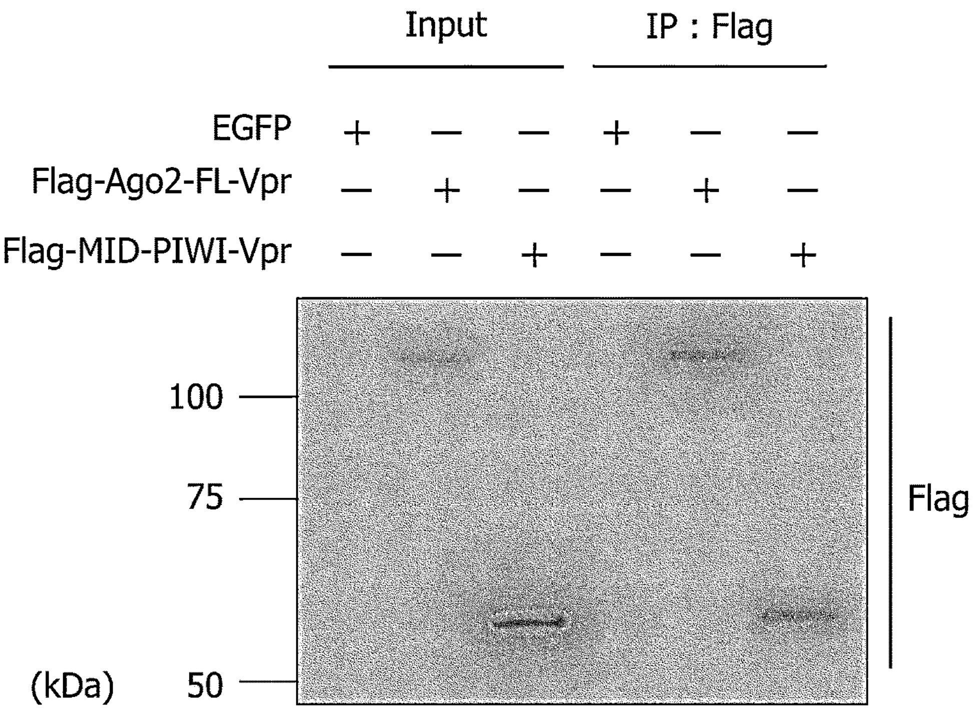
FIG. 3 shows results of immunoprecipitation of Flag-Ago2-FL-Vpr or Flag-MID-PIWI-Vpr with an anti-Flag antibody.

Dynabeads Protein G (Veritas), which was washed with Wash Buffer (HEPES (10 mM) pH 7.5, NaCl (150 mM), 0.1% Triton-X) and reacted with an anti-Flag-M2 antibody (Sigma-Aldrich, F1804, 1:800 dilution) for 30 minutes at room temperature in advance, was added to the supernatant, and was incubated and rotated for 1 hour at 4° C. The beads were washed three times with Wash Buffer, and then 120 μl of Elution Buffer was added, mixed, and incubated for 5 minutes at 4° C. After that, a 100 μl of the supernatant was collected, and 100 μl of 2× SDS sample buffer was added thereto to obtain an immunoprecipitate sample. The cell solution before immunoprecipitation ("Input" in FIG. 3) and the immunoprecipitate ("IP: Flag" in FIG. 3) were subjected to Western blotting in the same procedure as in 1 above to confirm that the Flag-Ago2-FL-Vpr and Flag-MID-PIWI-Vpr mutants were immunoprecipitated (FIG. 3).

Next, the miRNA was purified from the immunoprecipitate by using the mirVana™ miRNA Isolation Kit (final volume of 50 μl). Reverse transcription reactions were performed to prepare cDNA by using 5 μl of miRNA solution, TaqMan™ MicroRNA Reverse Transcription Kit (Thermo Fisher), and TaqMan™ MicroRNA Assays (Thermo Fisher). Furthermore, qPCR was performed with TaqMan™ Universal Master Mix II, no UNG (Thermo Fisher) TaqMan™ MicroRNA Assays (Thermo Fisher) to quantify a cDNA of miRNA-let7a-5p. The level of the miRNA was defined as a relative value when the amount of miRNA in the immunoprecipitate sample prepared from EGFP-expressing cells was set to 1.

Figure 4:
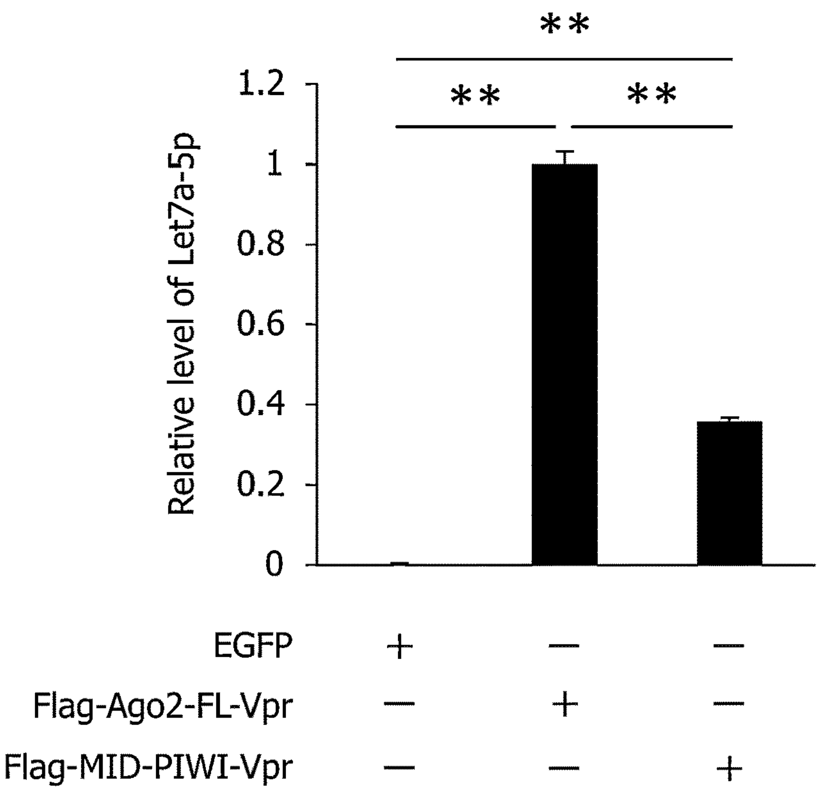
FIG. 4 is a graph showing relative quantification values of miRNA-let7a-5p co-precipitated with Flag-Ago2-FL-Vpr or Flag-MID-PIWI-Vpr.

Results are shown in FIG. 4. In the Figure, an asterisk (*) indicates p-values by one-way ANOVA with Tukey post-hoc test (** $p<0.01$). Error bars indicate standard deviations. The amount of miRNA-let7a-5p co-precipitated with Flag-MID-PIWI-Vpr was reduced as compared with the amount of miRNA-let7a-5p co-precipitated with Flag-Ago2-FL-Vpr, but was significantly greater than that of the negative control EGFP. These results indicate that the MID-PIWI-Vpr mutant binds to miRNA-let7a-5p.

Figure 5:
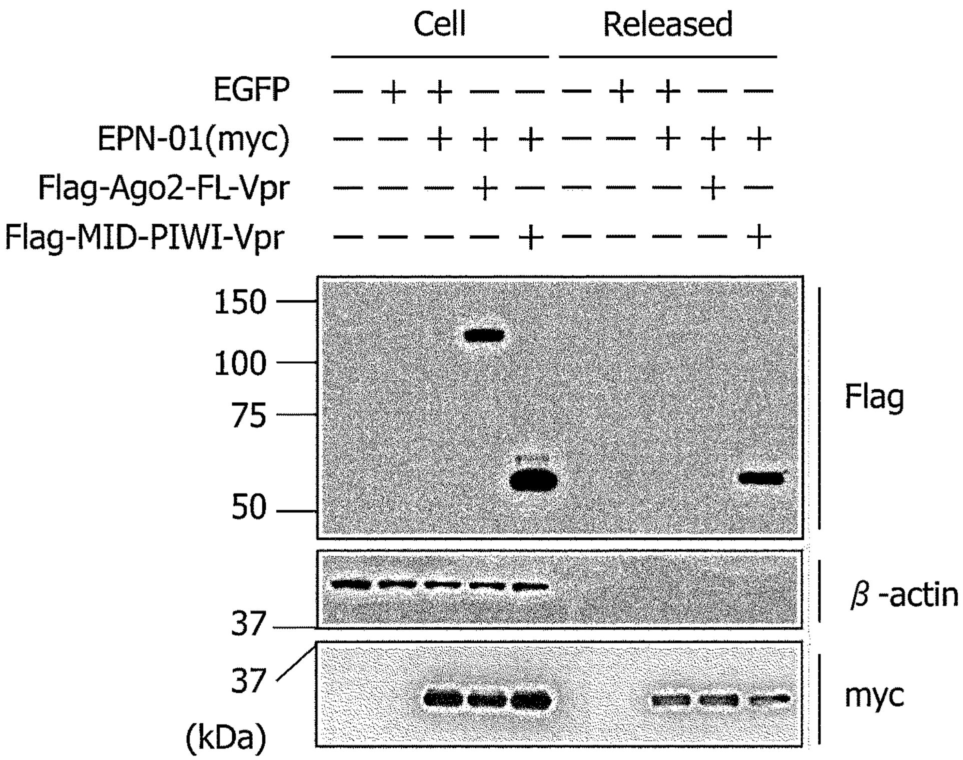
FIG. 5 shows results of Western blot analysis confirming Flag-Ago2-FL-Vpr or Flag-MID-PIWI-Vpr contained in cells and in extracellular vesicles.

3. Amount of miRNA-let7a-5p in Extracellular Vesicles Containing EPN-01/MID-PIWI-Vpr Mutant HEK293T cells co-expressing full-length Ago2 (Flag-Ago2-FL-Vpr) and EPN-01 or co-expressing Flag-MID-PIWI-Vpr and EPN-01 were prepared by the same procedure as in 1 above, and the cell solution and the extracellular-vesicle solution therefrom were subjected to Western blotting to confirm expression of proteins (FIG. 5). Only the MID-PIWI-Vpr mutant was detected from the extracellular-vesicle solution, as is the case with the result in FIG. 2.

Next, miRNA-let7a-5p in the extracellular-vesicle solution was purified and quantified by the same procedure as in 2 above. The level of the miRNA was defined as a relative value when the amount of the miRNA in the extracellular-vesicle solution prepared from untransfected cells was set to 1.

Figure 6:
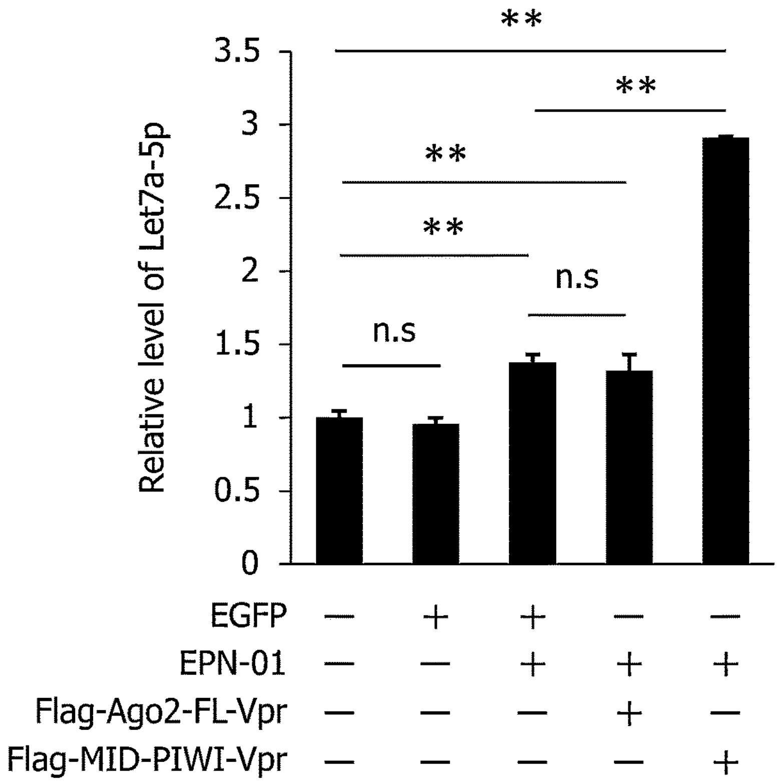
FIG. 6 is a graph showing relative quantification values of miRNA-let7a-5p in extracellular vesicle fractions obtained from HEK293T cells co-expressing Flag-Ago2-FL-Vpr or Flag-MID-PIWI-Vpr and EPN-01.

Results are shown in FIG. 6. In the Figure, an asterisk (*) indicates p-values by one-way ANOVA with Tukey post-hoc test (** $p<0.01$). Error bars indicate standard deviations. The yield of miRNA-let7a-5p from the extracellular-vesicle solution obtained from HEK293T cells co-expressing EPN-01 and Flag-MID-PIWI-Vpr was greatly increased. On the other hand, even when EPN-01 and Flag-Ago2-FL-Vpr were co-expressed, there was no significant increase in the yield of miRNA-let7a-5p as compared with the negative control in which EPN-01 and EGFP were co-expressed. These results indicate that co-expression of EPN-01 and MID-PIWI-Vpr mutant can increase miRNA-let7a-5p in an extracellular vesicle fraction.

4. Type and Amount of miRNA in EPN-01/MID-PIWI-Vpr Mutant-Containing Extracellular Vesicles Next-generation sequencing small RNA-seq was used to comprehensively identify miRNAs present in the extracellular vesicle fraction obtained from HEK293T cells co-expressing EPN-01 and Flag-MID-PIWI-Vpr. The extracellular vesicle fraction obtained from HEK293T cells without transfection and only with medium replacement was prepared as a control. As a result, 186 miRNAs were identified from the control extracellular vesicle fraction, and 323 miRNAs were identified from the extracellular vesicle fraction obtained from the EPN-01/MID-PIWI-Vpr co-expressing cells. Also, 145 miRNAs were commonly present in both the extracellular vesicle fractions, 41 miRNAs were present only in the control extracellular vesicle fraction, and 178 miRNAs were present only in the extracellular vesicle fraction obtained from the EPN-01/MID-PIWI-Vpr co-expressing cells. These results confirm that the types of miRNAs detectable from an extracellular vesicle fraction were increased by co-expression of EPN-01/MID-PIWI-Vpr.

Figure 7:
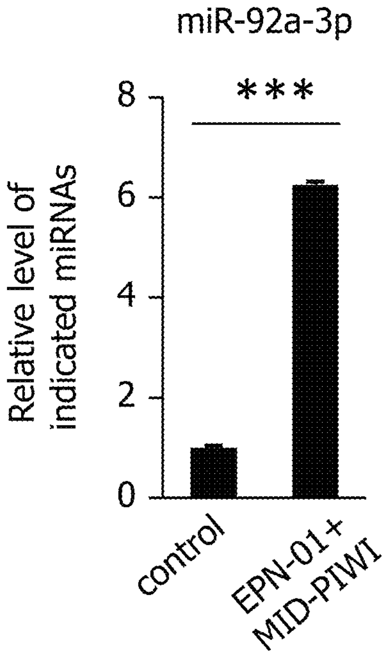
FIG. 7 is a graph showing relative quantification values of miR-92a-3p in extracellular vesicle fractions obtained from HEK293T cells co-expressing Flag-MID-PIWI-Vpr and EPN-01.
Figure 8:
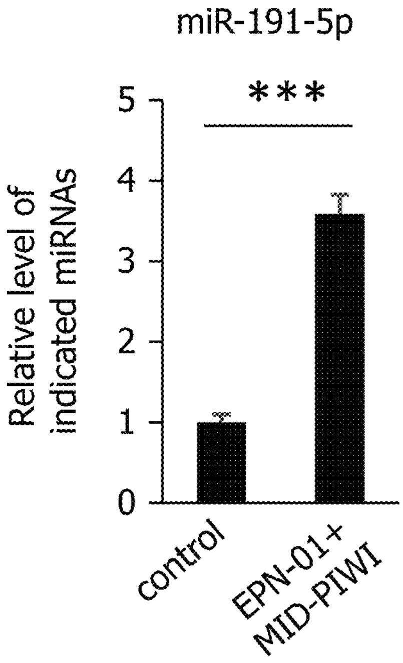
FIG. 8 is a graph showing relative quantification values of miR-191-5p in extracellular vesicle fractions obtained from HEK293T cells co-expressing Flag-MID-PIWI-Vpr and EPN-01.
Figure 9:
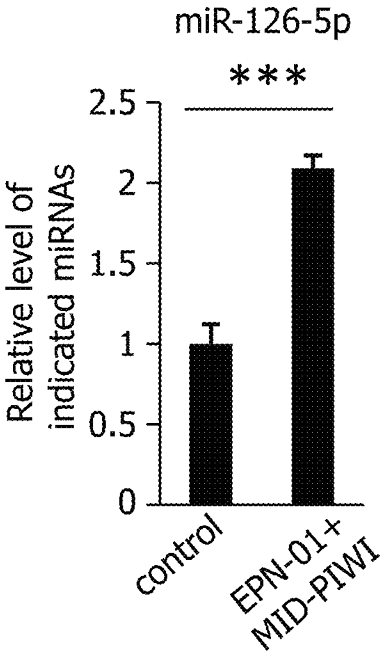
FIG. 9 is a graph showing relative quantification values of miR-126-5p in extracellular vesicle fractions obtained from HEK293T cells co-expressing Flag-MID-PIWI-Vpr and EPN-01.

Next, miR-92a-3p, miR-191-5p, and miR-126-5p, which were commonly detected in large amounts in the control and the extracellular vesicle fraction obtained from the EPN-01/MID-PIWI-Vpr co-expressing cells, were quantified by RT-qPCR by the same procedure as in 2 above. Results are shown in FIGS. 7 to 9. In the Figures, an asterisk (*) indicates p-values by Student's t-test (*** $p<0.001$). Error bars indicate standard deviations. It was confirmed that the yields of all miRNAs were increased by co-expression of EPN-01/MID-PIWI-Vpr.

Figure 10:
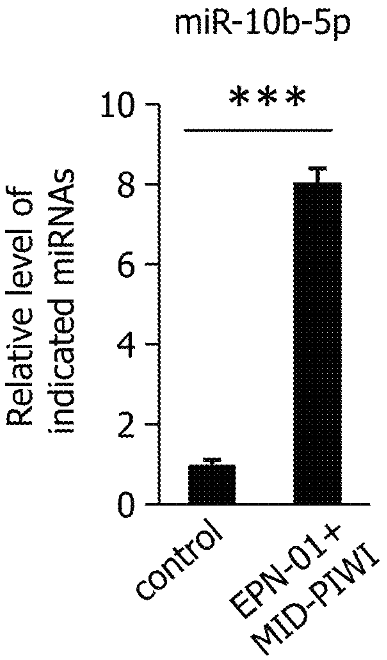
FIG. 10 is a graph showing relative quantification values of miR-10b-5p in extracellular vesicle fractions obtained from HEK293T cells co-expressing Flag-MID-PIWI-Vpr and EPN-01.

Furthermore, FIG. 10 shows the results regarding miR-10b-5p, which was found only in the extracellular vesicle fraction from EPN-01/MID-PIWI-Vpr co-expressing cells in small RNA-seq analysis. In the Figure, an asterisk (*) indicates p-values by Student's t-test (*** $p<0.001$). Error bars indicate standard deviations. RT-qPCR confirms that although miR-10b-5p was present in the control extracellular vesicle fraction, more than 8-fold more miR-10b-5p was present in the extracellular vesicle fraction from the EPN-01/MID-PIWI-Vpr co-expressing cells.

The above results indicate that co-expression of EPN-01 and MID-PIWI-Vpr mutant can increase the amount of a wide variety of miRNAs in the extracellular vesicle fraction, and it may be possible to analyze even trace amounts of miRNA that cannot be detected from normal exosomes.

5. Nondestructive Analysis of Cells Using EPN-01/MID-PIWI-Vpr Mutant-Containing Extracellular Vesicles It is known that the expression of miR-210 is strongly induced under hypoxic conditions. One of the well-studied hypoxia signaling pathways is controlled by hypoxia-inducible factor (HIF). Under normoxic conditions, HIF1a is hydroxylated, bound to the E3 ligase, and degraded by the proteasome. In contrast, under hypoxic conditions, HIF1a is stabilized, translocates to the nucleus without degradation, forms a dimer with HIF1B, and promotes transcription of target genes including miR-210 (Genes Dev. 2004 Sep. 15; 18(18):2183-94. doi: 10.1101/gad.1243304., Mol Cell. 2009 Sep. 24; 35(6):856-67. doi: 10.1016/j.molcel.2009.09.006.).

Western blotting was performed on the cell solution and the extracellular-vesicle solution by the same procedure as in 1 above to confirm protein expression, except that $CoCl_2$ (50 μM) was added six hours after transfection of the MID-PIWI-Vpr expression vector and the EPN-01 expression vector to induce hypoxia. Anti-HIF-1α antibody [EP1215Y] (Abcam, ab51608, 1:1000 dilution) was used to detect HIF1α.

Figure 11:
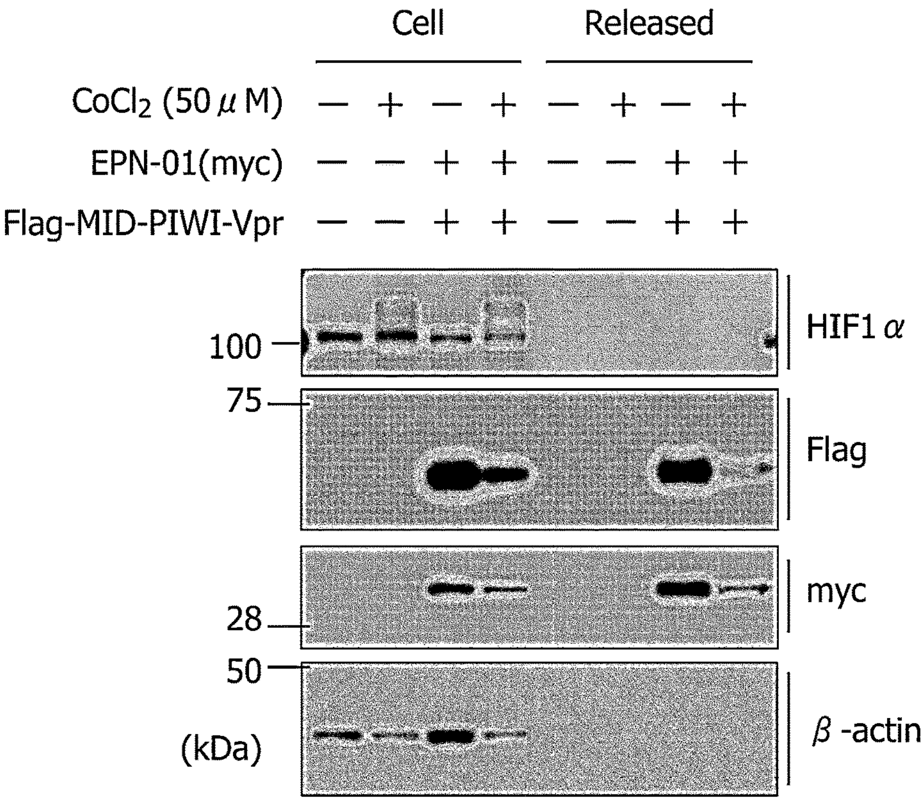
FIG. 11 is a diagram showing results of Western blot analysis confirming changes in the expression levels of HIF1α, EPN-01, and MID-PIWI-Vpr due to $CoCl_2$ treatment.

Results are shown in FIG. 11. Accumulation of HIF 1α was observed in cells treated with $CoCl_2$. These results are consistent with reports that HIF1a accumulates when hypoxia is induced by $CoCl_2$ treatment (Biol Res. 2019 Mar. 15; 52(1): 12. doi: 10.1186/s40659-019-0221-z.). Also, the expression levels of EPN-01 and MID-PIWI-Vpr decreased in $CoCl_2$-treated cells, and these results are consistent with reports that protein production is inhibited under hypoxic conditions (Mol Cell Biol. 2006 May; 26(10):3955-65. doi: 10.1128/MCB.26.10.3955-3965.2006.). Similarly, the yields of EPN-01 and MID-PIWI-Vpr in the extracellular vesicle fraction also decreased.

Next, miR-210 in the cell solution and the extracellular-vesicle solution was purified and quantified by the same procedure as in 2 above. As controls, the cell solution and the extracellular-vesicle fraction obtained from HEK293T cells without transfection and only with medium replacement were prepared. In addition, for comparison, miR-1303, which has not been reported to be associated with a hypoxic condition, was similarly purified and quantified.

Figure 12:
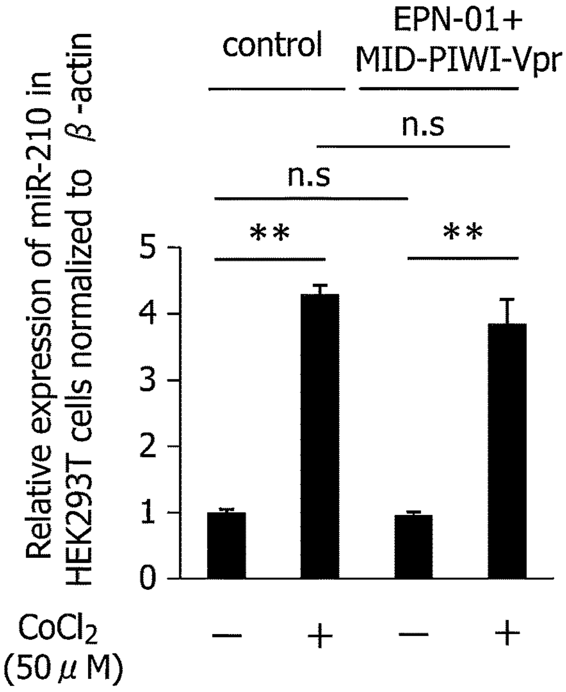
FIG. 12 is a graph showing changes due to $CoCl_2$ treatment in the expression level of miR-210 in HEK293T cells transfected with or without Flag-MID-PIWI-Vpr and EPN-01.
Figure 13:
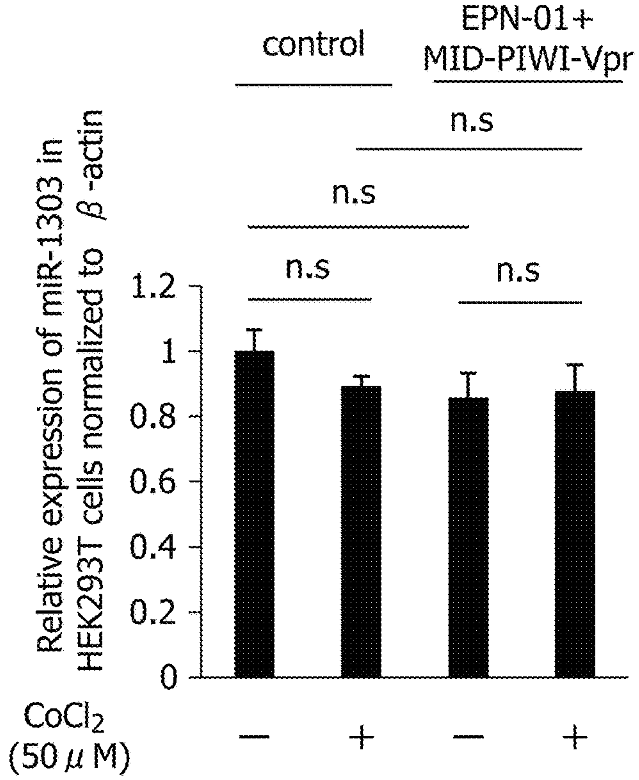
FIG. 13 is a graph showing changes due to $CoCl_2$ treatment in the expression level of miR-1303 in HEK293T cells transfected with or without Flag-MID-PIWI-Vpr and EPN-01.

Quantification results of miR-210 in cells are shown in FIG. 12, and quantification results of miR-210 in cells are shown in FIG. 13. In the Figures, an asterisk (*) indicates p-values by one-way ANOVA with Tukey post-hoc test (** $p<0.01$). Error bars indicate standard deviations. $CoCl_2$ treatment increased the expression level of miR-210, but did not significantly change the expression level of miR-1303. Also, no effect of co-expression of EPN-01 and MID-PIWI-Vpr was observed on the expression of either miRNA.

Figure 14:
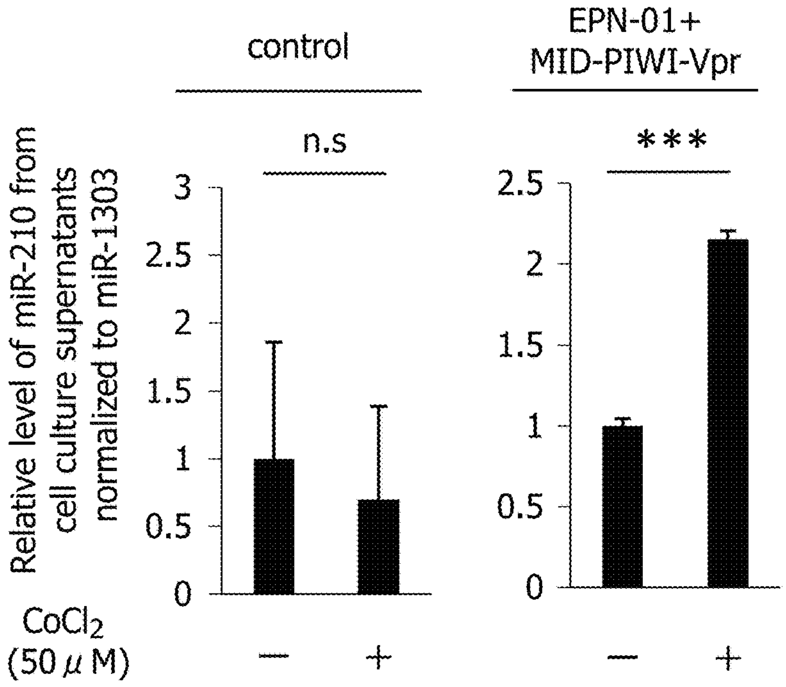
FIG. 14 is a graph showing changes due to $CoCl_2$ treatment in the content of miR-210 in extracellular vesicle fractions obtained from HEK293T cells transfected or not transfected with Flag-MID-PIWI-Vpr and EPN-01.

As confirmed above, $CoCl_2$ treatment reduced the expression levels of EPN-01 and MID-PIWI-Vpr in cells, which was assumed to reduce extracellular vesicles and miRNAs encapsulated therein. Thus, the quantification results of miR-210 normalized based on the quantification results of miR-1303 are shown in FIG. 14. In the Figure, an asterisk (*) indicates p-values by Student's t-test (*** $p<0.001$). Error bars indicate standard deviations. In the extracellular-vesicle fraction from control cells, no significant increase in miR-210 levels was observed due to $CoCl_2$ treatment. On the other hand, in the extracellular-vesicle fraction from cells co-expressing EPN-01 and MID-PIWI-Vpr, a significant increase in miR-210 levels was observed due to $CoCl_2$ treatment. These results indicate that co-expression of EPN-01 and MID-PIWI-Vpr enabled the detection of increased miR-210 expression due to $CoCl_2$ treatment with high accuracy.

The above results indicate that co-expression of EPN-01 and MID-PIWI-Vpr in cells enables miRNA analysis, without destroying the cells, with higher accuracy and sensitivity than conventional miRNA analysis using an exosome.

6. EPN-01/MID-PIWI-Vpr Co-Expression Increases Extracellular Vesicle Size and Production Volume By the same procedure as in 1 above, HEK293T cells co-expressing EPN-01 and Flag-MID-PIWI-Vpr and HEK293T cells co-expressing EPN-01 and EGFP were prepared, and extracellular-vesicle fractions were obtained from the culture supernatant by sucrose cushion centrifugation. Untransfected HEK293T cells were used as a control. Nanoparticle tracking analysis (NTA) was performed under the following conditions by using Nanosite NS300 (Malvern Panalytical). The camera level was set to 16 for all recordings. The extracellular-vesicle fractions were diluted 1:100 to 1:1000 with PBS to prepare measurement samples in such a way as to have a number of particles of $1\times10^8$ to $1\times 109$/ml. The camera focus was adjusted such that particles appeared as sharp individual dots. A 60-second image was recorded 5 times for each measurement sample. All data acquisition functions were set to automatic except the detection threshold was set to 8.

Figure 15:
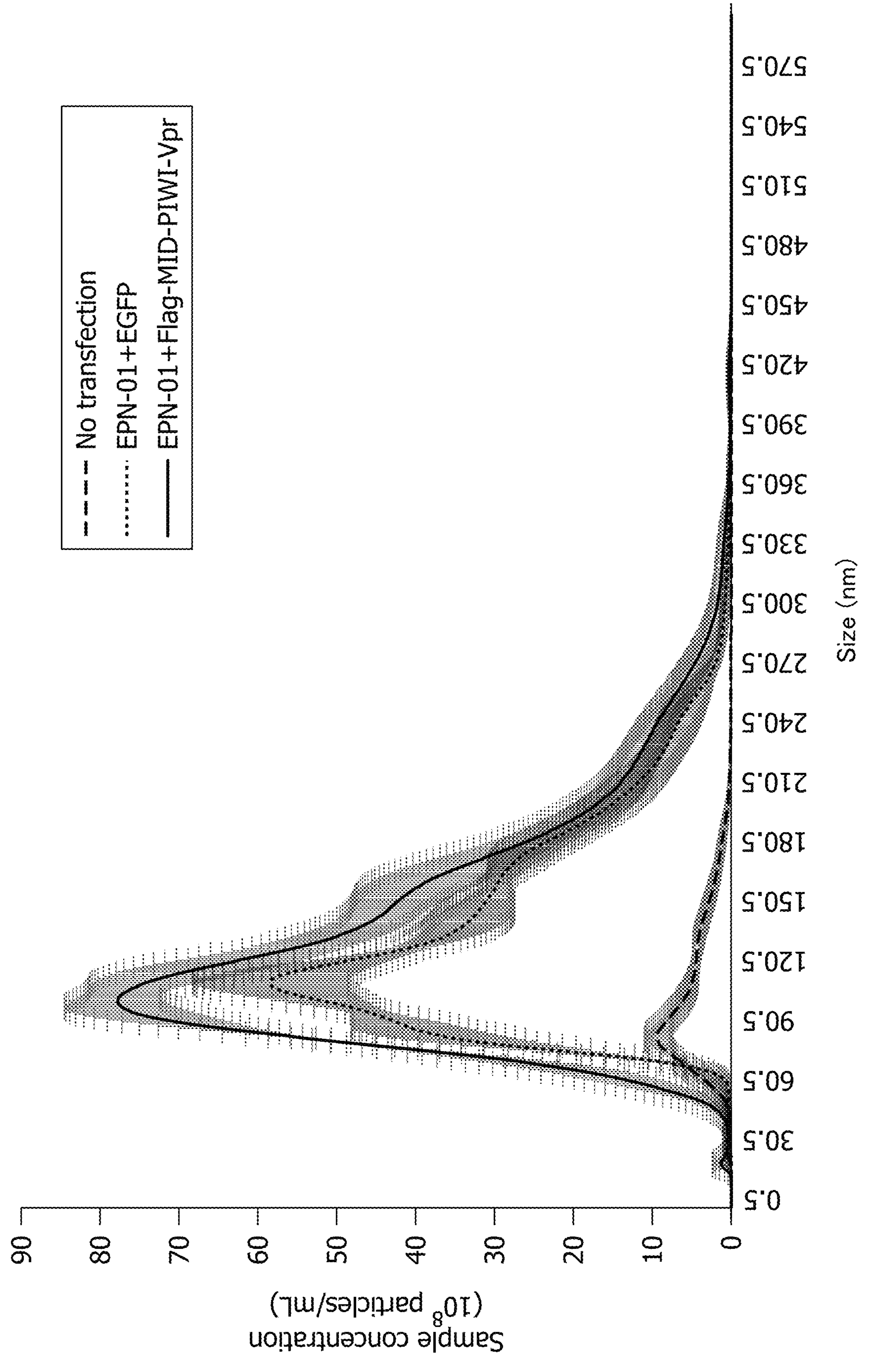
FIG. 15 is a graph showing vesicle concentrations and particle size distributions in extracellular vesicle fractions obtained from HEK293T cells co-expressing Flag-MID-PIWI-Vpr and EPN-01, HEK293T cells co-expressing EGFP and EPN-01, or untransfected HEK293T cells.

The particle size distributions and the concentrations of extracellular vesicles are shown in FIG. 15. Error bars indicate standard errors. Both the HEK293T cells co-expressing EPN-01 and Flag-MID-PIWI-Vpr and the HEK293T cells co-expressing EPN-01 and EGFP had increased numbers of extracellular vesicles as compared with the untransfected HEK293T cells. Also, both the HEK293T cells co-expressing EPN-01 and Flag-MID-PIWI-Vpr and the HEK293T cells co-expressing EPN-01 and EGFP had similar trends in the particle size distribution of extracellular vesicles.

Figure 16:
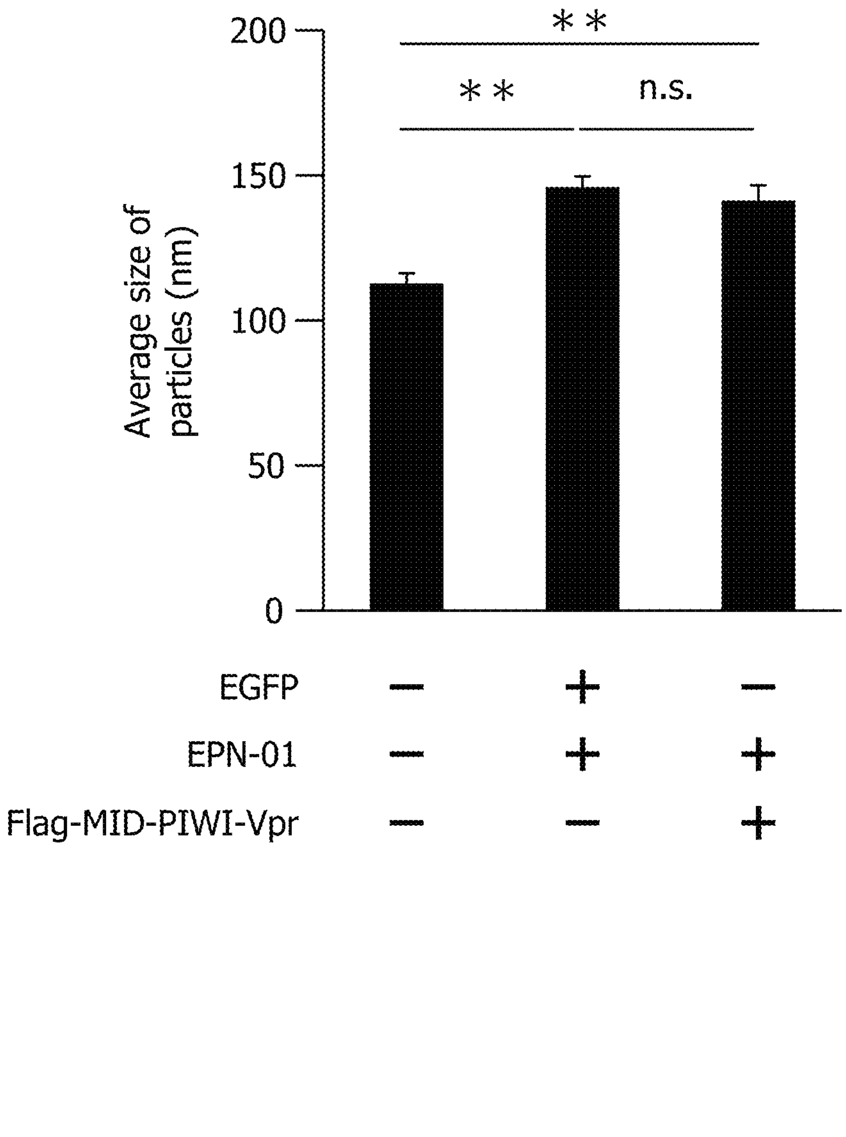
FIG. 16 is a graph showing the particle sizes (average values) of extracellular vesicles obtained from HEK293T cells co-expressing Flag-MID-PIWI-Vpr and EPN-01, HEK293T cells co-expressing EGFP and EPN-01, or untransfected HEK293T cells.

The average values of the particle sizes of extracellular vesicles are shown in FIG. 16. In the Figure, an asterisk (*) indicates p-values by one-way ANOVA with Tukey post-hoc test (** $p<0.01$). Error bars indicate standard errors. Both the HEK293T cells co-expressing EPN-01 and Flag-MID-PIWI-Vpr and the HEK293T cells co-expressing EPN-01 and EGFP tended to increase in the particle size of extracellular vesicles.

The above results indicate that extracellular vesicles that are larger than normal exosomes can be obtained at a high concentration from cells co-expressing EPN-01 and the MID-PIWI-Vpr mutant.

The invention claimed is:

1. A method for noninvasively acquiring a microRNA from an in vitro cell, the method comprising:

(1) introducing a nucleic acid coding a microRNA-binding protein and a nucleic acid encoding a vesicle-forming protein into the cell, wherein the microRNA-binding protein comprises a first portion consisting of an MID domain and a PIWI domain of an Argonaute protein and a second portion consisting of a virus protein R, and the vesicle-forming protein comprises: a palmitoylation or myristoylation signal or a pleckstrin homology domain; a self-assembling domain; an ESCRT or ESCRT-related factor-binding domain; and a Gag p6 domain; thereby producing an exosome-like vesicle comprising a microRNA, (2) collecting an extracellular fluid of the cell, and (3) extracting the micro-RNA from the extracellular fluid.

2. The method according to claim 1, wherein the microRNA-binding protein comprises an amino acid sequence having at least 90% identity to the amino acid sequence of SEQ ID NO: 1.

3. The method according to claim 2, wherein the vesicle-forming protein comprises an amino acid sequence having at least 90% identity to an amino acid sequence selected from the group consisting of SEQ ID NOs: 2 to 6.

4. The method according to claim 2, wherein the extracellular fluid is a culture supernatant.

5. The method according to claim 1, wherein the vesicle-forming protein comprises an amino acid sequence having at least 90% identity to an amino acid sequence selected from the group consisting of SEQ ID NOs: 2 to 6.

6. The method according to claim 5, wherein the extracellular fluid is a culture supernatant.

7. The method according to claim 1, wherein the extracellular fluid is a culture supernatant.

8. An exosome-like vesicle comprising:

(a) a microRNA, (b) a microRNA-binding protein comprising a first portion consisting of an MID domain and a PIWI domain of an Argonaute protein and a second portion consisting of a virus protein R, and (c) a nanocage composed of a vesicle-forming protein comprising an amino acid sequence having at least 90% identity to an amino acid sequence selected from the group consisting of SEQ ID NOs: 2 to 6.

9. The exosome-like vesicle according to claim 8, further comprising (d) a membrane fusion protein.

* * * * *

SEQUENCE LISTING

```
<160> NUMBER OF SEQ ID NOS: 26

<210> SEQ ID NO 1
<211> LENGTH: 522
<212> TYPE: PRT
```

<213> ORGANISM: Artificial Sequence
<220> FEATURE:
<223> OTHER INFORMATION: microRNA binding protein

<400> SEQUENCE: 1

Ile Glu Ile Lys Val Trp Ala Ile Ala Cys Phe Ala Pro Gln Arg Gln
1 5 10 15

Cys Thr Glu Val His Leu Lys Ser Phe Thr Glu Gln Leu Arg Lys Ile
20 25 30

Ser Arg Asp Ala Gly Met Pro Ile Gln Gly Gln Pro Cys Phe Cys Lys
35 40 45

Tyr Ala Gln Gly Ala Asp Ser Val Glu Pro Met Phe Arg His Leu Lys
50 55 60

Asn Thr Tyr Ala Gly Leu Gln Leu Val Val Val Ile Leu Pro Gly Lys
65 70 75 80

Thr Pro Val Tyr Ala Glu Val Lys Arg Val Gly Asp Thr Val Leu Gly
85 90 95

Met Ala Thr Gln Cys Val Gln Met Lys Asn Val Gln Arg Thr Thr Pro
100 105 110

Gln Thr Leu Ser Asn Leu Cys Leu Lys Ile Asn Val Lys Leu Gly Gly
115 120 125

Val Asn Asn Ile Leu Leu Pro Gln Gly Arg Pro Pro Val Phe Gln Gln
130 135 140

Pro Val Ile Phe Leu Gly Ala Asp Val Thr His Pro Pro Ala Gly Asp
145 150 155 160

Gly Lys Lys Pro Ser Ile Ala Ala Val Val Gly Ser Met Asp Ala His
165 170 175

Pro Asn Arg Tyr Cys Ala Thr Val Arg Val Gln Gln His Arg Gln Glu
180 185 190

Ile Ile Gln Asp Leu Ala Ala Met Val Arg Glu Leu Leu Ile Gln Phe
195 200 205

Tyr Lys Ser Thr Arg Phe Lys Pro Thr Arg Ile Ile Phe Tyr Arg Asp
210 215 220

Gly Val Ser Glu Gly Gln Phe Gln Gln Val Leu His His Glu Leu Leu
225 230 235 240

Ala Ile Arg Glu Ala Cys Ile Lys Leu Glu Lys Asp Tyr Gln Pro Gly
245 250 255

Ile Thr Phe Ile Val Val Gln Lys Arg His His Thr Arg Leu Phe Cys
260 265 270

Thr Asp Lys Asn Glu Arg Val Gly Lys Ser Gly Asn Ile Pro Ala Gly
275 280 285

Thr Thr Val Asp Thr Lys Ile Thr His Pro Thr Glu Phe Asp Phe Tyr
290 295 300

Leu Cys Ser His Ala Gly Ile Gln Gly Thr Ser Arg Pro Ser His Tyr
305 310 315 320

His Val Leu Trp Asp Asp Asn Arg Phe Ser Ser Asp Glu Leu Gln Ile
325 330 335

Leu Thr Tyr Gln Leu Cys His Thr Tyr Val Arg Cys Thr Arg Ser Val
340 345 350

Ser Ile Pro Ala Pro Ala Tyr Tyr Ala His Leu Val Ala Phe Arg Ala
355 360 365

Arg Tyr His Leu Val Asp Lys Glu His Asp Ser Ala Glu Gly Ser His
370 375 380

Thr Ser Gly Gln Ser Asn Gly Arg Asp His Gln Ala Leu Ala Lys Ala 385 390 395 400

Val Gln Val His Gln Asp Thr Leu Arg Thr Met Tyr Phe Ala Ser Arg
405 410 415

Leu Glu Asp Ile Gly Gly Gly Gly Gly Gly Glu Gln Ala Pro Glu Asp
420 425 430

Gln Gly Pro Gln Arg Glu Pro His Asn Glu Trp Thr Leu Glu Leu Leu
435 440 445

Glu Glu Leu Lys Arg Glu Ala Val Arg His Phe Pro Arg Pro Trp Leu
450 455 460

His Gly Leu Gly Gln His Ile Tyr Glu Thr Tyr Gly Asp Thr Trp Ala
465 470 475 480

Gly Val Glu Ala Ile Ile Arg Ile Leu Gln Gln Leu Leu Phe Ile His
485 490 495

Phe Arg Ile Gly Cys Gln His Ser Arg Ile Gly Ile Ile Gln Gln Arg
500 505 510

Arg Ala Arg Arg Asn Gly Ala Ser Arg Ser
515 520

<210> SEQ ID NO 2
<211> LENGTH: 282
<212> TYPE: PRT
<213> ORGANISM: Artificial Sequence
<220> FEATURE:
<223> OTHER INFORMATION: EPN-01

<400> SEQUENCE: 2

Met Gly Ala Arg Ala Ser Gly Ser Lys Ser Gly Ser Gly Ser Asp Ser
1 5 10 15

Gly Ser Lys Ile Glu Glu Leu Phe Lys Lys His Lys Ile Val Ala Val
20 25 30

Leu Arg Ala Asn Ser Val Glu Glu Ala Lys Lys Lys Ala Leu Ala Val
35 40 45

Phe Leu Gly Gly Val His Leu Ile Glu Ile Thr Phe Thr Val Pro Asp
50 55 60

Ala Asp Thr Val Ile Lys Glu Leu Ser Phe Leu Lys Glu Met Gly Ala
65 70 75 80

Ile Ile Gly Ala Gly Thr Val Thr Ser Val Glu Gln Cys Arg Lys Ala
85 90 95

Val Glu Ser Gly Ala Glu Phe Ile Val Ser Pro His Leu Asp Glu Glu
100 105 110

Ile Ser Gln Phe Cys Lys Glu Lys Gly Val Phe Tyr Met Pro Gly Val
115 120 125

Met Thr Pro Thr Glu Leu Val Lys Ala Met Lys Leu Gly His Thr Ile
130 135 140

Leu Lys Leu Phe Pro Gly Glu Val Val Gly Pro Gln Phe Val Lys Ala
145 150 155 160

Met Lys Gly Pro Phe Pro Asn Val Lys Phe Val Pro Thr Gly Gly Val
165 170 175

Asn Leu Asp Asn Val Cys Glu Trp Phe Lys Ala Gly Val Leu Ala Val
180 185 190

Gly Val Gly Ser Ala Leu Val Lys Gly Thr Pro Val Glu Val Ala Glu
195 200 205

Lys Ala Lys Ala Phe Val Glu Lys Ile Arg Gly Cys Thr Glu Gln Lys
210 215 220

Leu Ile Ser Glu Glu Asp Leu Gln Ser Arg Pro Glu Pro Thr Ala Pro

```
225                 230                 235                 240

Pro Glu Glu Ser Phe Arg Ser Gly Val Glu Thr Thr Thr Pro Pro Gln
                245                 250                 255

Lys Gln Glu Pro Ile Asp Lys Glu Leu Tyr Pro Leu Thr Ser Leu Arg
            260                 265                 270

Ser Leu Phe Gly Asn Asp Pro Ser Ser Gln
        275                 280


<210> SEQ ID NO 3
<211> LENGTH: 281
<212> TYPE: PRT
<213> ORGANISM: Artificial Sequence
<220> FEATURE:
<223> OTHER INFORMATION: EPN-03

<400> SEQUENCE: 3

Met Gly Ala Gln Phe Ser Gly Ser Lys Ser Gly Ser Gly Ser Asp Ser
1               5                   10                  15

Gly Ser Lys Ile Glu Glu Leu Phe Lys Lys His Lys Ile Val Ala Val
            20                  25                  30

Leu Arg Ala Asn Ser Val Glu Glu Ala Lys Lys Lys Ala Leu Ala Val
        35                  40                  45

Phe Leu Gly Gly Val His Leu Ile Glu Ile Thr Phe Thr Val Pro Asp
    50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
    130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
            180                 185                 190

Gly Val Gly Ser Ala Leu Val Lys Gly Thr Pro Val Glu Val Ala Glu
        195                 200                 205

Lys Ala Lys Ala Phe Val Glu Lys Ile Arg Gly Cys Thr Glu Gln Lys
    210                 215                 220

Leu Ile Ser Glu Glu Asp Leu Gln Ser Arg Pro Glu Pro Thr Ala Pro
225                 230                 235                 240

Pro Glu Glu Ser Phe Arg Ser Gly Val Glu Thr Thr Thr Pro Pro Gln
                245                 250                 255

Lys Gln Glu Pro Ile Asp Lys Glu Leu Tyr Pro Leu Thr Ser Leu Arg
            260                 265                 270

Ser Leu Phe Gly Asn Asp Pro Ser Ser
        275                 280


<210> SEQ ID NO 4
<211> LENGTH: 288
<212> TYPE: PRT
```

<213> ORGANISM: Artificial Sequence
<220> FEATURE:
<223> OTHER INFORMATION: EPN-07

<400> SEQUENCE: 4

```
Met Gly Cys Ile Lys Ser Lys Arg Lys Asp Asn Leu Asn Gly Ser Lys
1               5                   10                  15

Ser Gly Ser Gly Ser Asp Ser Gly Ser Lys Ile Glu Glu Leu Phe Lys
            20                  25                  30

Lys His Lys Ile Val Ala Val Leu Arg Ala Asn Ser Val Glu Glu Ala
        35                  40                  45

Lys Lys Lys Ala Leu Ala Val Phe Leu Gly Gly Val His Leu Ile Glu
    50                  55                  60

Ile Thr Phe Thr Val Pro Asp Ala Asp Thr Val Ile Lys Glu Leu Ser
65                  70                  75                  80

Phe Leu Lys Glu Met Gly Ala Ile Ile Gly Ala Gly Thr Val Thr Ser
                85                  90                  95

Val Glu Gln Cys Arg Lys Ala Val Glu Ser Gly Ala Glu Phe Ile Val
            100                 105                 110

Ser Pro His Leu Asp Glu Glu Ile Ser Gln Phe Cys Lys Glu Lys Gly
        115                 120                 125

Val Phe Tyr Met Pro Gly Val Met Thr Pro Thr Glu Leu Val Lys Ala
    130                 135                 140

Met Lys Leu Gly His Thr Ile Leu Lys Leu Phe Pro Gly Glu Val Val
145                 150                 155                 160

Gly Pro Gln Phe Val Lys Ala Met Lys Gly Pro Phe Pro Asn Val Lys
                165                 170                 175

Phe Val Pro Thr Gly Gly Val Asn Leu Asp Asn Val Cys Glu Trp Phe
            180                 185                 190

Lys Ala Gly Val Leu Ala Val Gly Val Gly Ser Ala Leu Val Lys Gly
        195                 200                 205

Thr Pro Val Glu Val Ala Glu Lys Ala Lys Ala Phe Val Glu Lys Ile
    210                 215                 220

Arg Gly Cys Thr Glu Gln Lys Leu Ile Ser Glu Glu Asp Leu Gln Ser
225                 230                 235                 240

Arg Pro Glu Pro Thr Ala Pro Pro Glu Glu Ser Phe Arg Ser Gly Val
                245                 250                 255

Glu Thr Thr Thr Pro Pro Gln Lys Gln Glu Pro Ile Asp Lys Glu Leu
            260                 265                 270

Tyr Pro Leu Thr Ser Leu Arg Ser Leu Phe Gly Asn Asp Pro Ser Ser
        275                 280                 285
```

<210> SEQ ID NO 5
<211> LENGTH: 282
<212> TYPE: PRT
<213> ORGANISM: Artificial Sequence
<220> FEATURE:
<223> OTHER INFORMATION: EPN-08

<400> SEQUENCE: 5

```
Met Gly Cys Thr Leu Ser Ala Glu Glu Arg Ala Ala Leu Gly Ser Lys
1               5                   10                  15

Ser Gly Ser Gly Ser Asp Ser Gly Ser Lys Ile Glu Glu Leu Phe Lys
            20                  25                  30

Lys His Lys Ile Val Ala Val Leu Arg Ala Asn Ser Val Glu Glu Ala
        35                  40                  45
```

```
Lys Lys Lys Ala Leu Ala Val Phe Leu Gly Gly Val His Leu Ile Glu
    50                  55                  60

Ile Thr Phe Thr Val Pro Asp Ala Asp Thr Val Ile Lys Glu Leu Ser
65                  70                  75                  80

Phe Leu Lys Glu Met Gly Ala Ile Ile Gly Ala Gly Thr Val Thr Ser
                85                  90                  95

Val Glu Gln Cys Arg Lys Ala Val Glu Ser Gly Ala Glu Phe Ile Val
            100                 105                 110

Ser Pro His Leu Asp Glu Glu Ile Ser Gln Phe Cys Lys Glu Lys Gly
        115                 120                 125

Val Phe Tyr Met Pro Gly Val Met Thr Pro Thr Glu Leu Val Lys Ala
    130                 135                 140

Met Lys Leu Gly His Thr Ile Leu Lys Leu Phe Pro Gly Glu Val Val
145                 150                 155                 160

Gly Pro Gln Phe Val Lys Ala Met Lys Gly Pro Phe Pro Asn Val Lys
                165                 170                 175

Phe Val Pro Thr Gly Gly Val Asn Leu Asp Asn Val Cys Glu Trp Phe
            180                 185                 190

Lys Ala Gly Val Leu Ala Val Gly Val Gly Ser Ala Leu Val Lys Gly
        195                 200                 205

Thr Pro Val Glu Val Ala Glu Lys Ala Lys Ala Phe Val Glu Lys Ile
    210                 215                 220

Arg Gly Cys Thr Glu Gln Lys Leu Ile Ser Glu Glu Asp Leu Gln Ser
225                 230                 235                 240

Arg Pro Glu Pro Thr Ala Pro Pro Glu Glu Ser Phe Arg Ser Gly Val
                245                 250                 255

Glu Thr Thr Thr Pro Pro Gln Lys Gln Glu Pro Ile Asp Lys Glu Leu
            260                 265                 270

Tyr Pro Leu Thr Ser Leu Arg Ser Leu Phe
        275                 280


<210> SEQ ID NO 6
<211> LENGTH: 399
<212> TYPE: PRT
<213> ORGANISM: Artificial Sequence
<220> FEATURE:
<223> OTHER INFORMATION: EPN-018

<400> SEQUENCE: 6

Met His Gly Leu Gln Asp Asp Pro Asp Leu Gln Ala Leu Leu Lys Gly
1               5                   10                  15

Ser Gln Leu Leu Lys Val Lys Ser Ser Ser Trp Arg Arg Glu Arg Phe
            20                  25                  30

Tyr Lys Leu Gln Glu Asp Cys Lys Thr Ile Trp Gln Glu Ser Arg Lys
        35                  40                  45

Val Met Arg Ser Pro Glu Ser Gln Leu Phe Ser Ile Glu Asp Ile Gln
    50                  55                  60

Glu Val Arg Met Gly His Arg Thr Glu Gly Leu Glu Lys Phe Ala Arg
65                  70                  75                  80

Asp Ile Pro Glu Asp Arg Cys Phe Ser Ile Val Phe Lys Asp Gln Arg
                85                  90                  95

Asn Thr Leu Asp Leu Ile Ala Pro Ser Pro Ala Asp Ala Gln His Trp
            100                 105                 110

Val Gln Gly Leu Arg Lys Ile Ile His His Ser Gly Ser Met Asp Gln
        115                 120                 125
```

```
Arg Gln Lys Gly Ser Gly Ser Lys Ile Glu Glu Leu Phe Lys Lys His
    130                 135                 140

Lys Ile Val Ala Val Leu Arg Ala Asn Ser Val Glu Glu Ala Lys Lys
145                 150                 155                 160

Lys Ala Leu Ala Val Phe Leu Gly Gly Val His Leu Ile Glu Ile Thr
                165                 170                 175

Phe Thr Val Pro Asp Ala Asp Thr Val Ile Lys Glu Leu Ser Phe Leu
            180                 185                 190

Lys Glu Met Gly Ala Ile Ile Gly Ala Gly Thr Val Thr Ser Val Glu
        195                 200                 205

Gln Cys Arg Lys Ala Val Glu Ser Gly Ala Glu Phe Ile Val Ser Pro
    210                 215                 220

His Leu Asp Glu Glu Ile Ser Gln Phe Cys Lys Glu Lys Gly Val Phe
225                 230                 235                 240

Tyr Met Pro Gly Val Met Thr Pro Thr Glu Leu Val Lys Ala Met Lys
                245                 250                 255

Leu Gly His Thr Ile Leu Lys Leu Phe Pro Gly Glu Val Val Gly Pro
            260                 265                 270

Gln Phe Val Lys Ala Met Lys Gly Pro Phe Pro Asn Val Lys Phe Val
        275                 280                 285

Pro Thr Gly Gly Val Asn Leu Asp Asn Val Cys Glu Trp Phe Lys Ala
    290                 295                 300

Gly Val Leu Ala Val Gly Val Gly Ser Ala Leu Val Lys Gly Thr Pro
305                 310                 315                 320

Val Glu Val Ala Glu Lys Ala Lys Ala Phe Val Glu Lys Ile Arg Gly
                325                 330                 335

Cys Thr Glu Gln Lys Leu Ile Ser Glu Glu Asp Leu Gln Ser Arg Pro
            340                 345                 350

Glu Pro Thr Ala Pro Pro Glu Glu Ser Phe Arg Ser Gly Val Glu Thr
        355                 360                 365

Thr Thr Pro Pro Gln Lys Gln Glu Pro Ile Asp Lys Glu Leu Tyr Pro
    370                 375                 380

Leu Thr Ser Leu Arg Ser Leu Phe Gly Asn Asp Pro Ser Ser Gln
385                 390                 395


<210> SEQ ID NO 7
<211> LENGTH: 858
<212> TYPE: PRT
<213> ORGANISM: Homo sapiens

<400> SEQUENCE: 7

Met Tyr Ser Gly Ala Gly Pro Ala Leu Ala Pro Pro Ala Pro Pro Pro
1               5                   10                  15

Pro Ile Gln Gly Tyr Ala Phe Lys Pro Pro Pro Arg Pro Asp Phe Gly
            20                  25                  30

Thr Ser Gly Arg Thr Ile Lys Leu Gln Ala Asn Phe Phe Glu Met Asp
        35                  40                  45

Ile Pro Lys Ile Asp Ile Tyr His Tyr Glu Leu Asp Ile Lys Pro Glu
    50                  55                  60

Lys Cys Pro Arg Arg Val Asn Arg Glu Ile Val Glu His Met Val Gln
65                  70                  75                  80

His Phe Lys Thr Gln Ile Phe Gly Asp Arg Lys Pro Val Phe Asp Gly
                85                  90                  95

Arg Lys Asn Leu Tyr Thr Ala Met Pro Leu Pro Ile Gly Arg Asp Lys
            100                 105                 110
```

```
Val Glu Leu Glu Val Thr Leu Pro Gly Glu Gly Lys Asp Arg Ile Phe
        115                 120                 125

Lys Val Ser Ile Lys Trp Val Ser Cys Val Ser Leu Gln Ala Leu His
    130                 135                 140

Asp Ala Leu Ser Gly Arg Leu Pro Ser Val Pro Phe Glu Thr Ile Gln
145                 150                 155                 160

Ala Leu Asp Val Val Met Arg His Leu Pro Ser Met Arg Tyr Thr Pro
                165                 170                 175

Val Gly Arg Ser Phe Phe Thr Ala Ser Glu Gly Cys Ser Asn Pro Leu
            180                 185                 190

Gly Gly Gly Arg Glu Val Trp Phe Gly Phe His Gln Ser Val Arg Pro
        195                 200                 205

Ser Leu Trp Lys Met Met Leu Asn Ile Asp Val Ser Ala Thr Ala Phe
    210                 215                 220

Tyr Lys Ala Gln Pro Val Ile Glu Phe Val Cys Glu Val Leu Asp Phe
225                 230                 235                 240

Lys Ser Ile Glu Glu Gln Gln Lys Pro Leu Thr Asp Ser Gln Arg Val
                245                 250                 255

Lys Phe Thr Lys Glu Ile Lys Gly Leu Lys Val Glu Ile Thr His Cys
            260                 265                 270

Gly Gln Met Lys Arg Lys Tyr Arg Val Cys Asn Val Thr Arg Arg Pro
        275                 280                 285

Ala Ser His Gln Thr Phe Pro Leu Gln Gln Glu Ser Gly Gln Thr Val
    290                 295                 300

Glu Cys Thr Val Ala Gln Tyr Phe Lys Asp Arg His Lys Leu Val Leu
305                 310                 315                 320

Arg Tyr Pro His Leu Pro Cys Leu Gln Val Gly Gln Glu Gln Lys His
                325                 330                 335

Thr Tyr Leu Pro Leu Glu Val Cys Asn Ile Val Ala Gly Gln Arg Cys
            340                 345                 350

Ile Lys Lys Leu Thr Asp Asn Gln Thr Ser Thr Met Ile Arg Ala Thr
        355                 360                 365

Ala Arg Ser Ala Pro Asp Arg Gln Glu Glu Ile Ser Lys Leu Met Arg
    370                 375                 380

Ser Ala Ser Phe Asn Thr Asp Pro Tyr Val Arg Glu Phe Gly Ile Met
385                 390                 395                 400

Val Lys Asp Glu Met Thr Asp Val Thr Gly Arg Val Leu Gln Pro Pro
                405                 410                 415

Ser Ile Leu Tyr Gly Gly Arg Asn Lys Ala Ile Ala Thr Pro Val Gln
            420                 425                 430

Gly Val Trp Asp Met Arg Asn Lys Gln Phe His Thr Gly Ile Glu Ile
        435                 440                 445

Lys Val Trp Ala Ile Ala Cys Phe Ala Pro Gln Arg Gln Cys Thr Glu
    450                 455                 460

Val His Leu Lys Ser Phe Thr Glu Gln Leu Arg Lys Ile Ser Arg Asp
465                 470                 475                 480

Ala Gly Met Pro Ile Gln Gly Gln Pro Cys Phe Cys Lys Tyr Ala Gln
                485                 490                 495

Gly Ala Asp Ser Val Glu Pro Met Phe Arg His Leu Lys Asn Thr Tyr
            500                 505                 510

Ala Gly Leu Gln Leu Val Val Val Ile Leu Pro Gly Lys Thr Pro Val
        515                 520                 525
```

-continued

Tyr Ala Glu Val Lys Arg Val Gly Asp Thr Val Leu Gly Met Ala Thr
530 535 540

Gln Cys Val Gln Met Lys Asn Val Gln Arg Thr Thr Pro Gln Thr Leu
545 550 555 560

Ser Asn Leu Cys Leu Lys Ile Asn Val Lys Leu Gly Gly Val Asn Asn
565 570 575

Ile Leu Leu Pro Gln Gly Arg Pro Pro Val Phe Gln Gln Pro Val Ile
580 585 590

Phe Leu Gly Ala Asp Val Thr His Pro Pro Ala Gly Asp Gly Lys Lys
595 600 605

Pro Ser Ile Ala Ala Val Val Gly Ser Met Asp Ala His Pro Asn Arg
610 615 620

Tyr Cys Ala Thr Val Arg Val Gln Gln His Arg Gln Glu Ile Ile Gln
625 630 635 640

Asp Leu Ala Ala Met Val Arg Glu Leu Leu Ile Gln Phe Tyr Lys Ser
645 650 655

Thr Arg Phe Lys Pro Thr Arg Ile Ile Phe Tyr Arg Asp Gly Val Ser
660 665 670

Glu Gly Gln Phe Gln Gln Val Leu His His Glu Leu Leu Ala Ile Arg
675 680 685

Glu Ala Cys Ile Lys Leu Glu Lys Asp Tyr Gln Pro Gly Ile Thr Phe
690 695 700

Ile Val Val Gln Lys Arg His His Thr Arg Leu Phe Cys Thr Asp Lys
705 710 715 720

Asn Glu Arg Val Gly Lys Ser Gly Asn Ile Pro Ala Gly Thr Thr Val
725 730 735

Asp Thr Lys Ile Thr His Pro Thr Glu Phe Asp Phe Tyr Leu Cys Ser
740 745 750

His Ala Gly Ile Gln Gly Thr Ser Arg Pro Ser His Tyr His Val Leu
755 760 765

Trp Asp Asp Asn Arg Phe Ser Ser Asp Glu Leu Gln Ile Leu Thr Tyr
770 775 780

Gln Leu Cys His Thr Tyr Val Arg Cys Thr Arg Ser Val Ser Ile Pro
785 790 795 800

Ala Pro Ala Tyr Tyr Ala His Leu Val Ala Phe Arg Ala Arg Tyr His
805 810 815

Leu Val Asp Lys Glu His Asp Ser Ala Glu Gly Ser His Thr Ser Gly
820 825 830

Gln Ser Asn Gly Arg Asp His Gln Ala Leu Ala Lys Ala Val Gln Val
835 840 845

His Gln Asp Thr Leu Arg Thr Met Tyr Phe
850 855

<210> SEQ ID NO 8
<211> LENGTH: 97
<212> TYPE: PRT
<213> ORGANISM: HIV-1

<400> SEQUENCE: 8

Met Glu Gln Ala Pro Glu Asp Gln Gly Pro Gln Arg Glu Pro His Asn
1 5 10 15

Glu Trp Thr Leu Glu Leu Leu Glu Glu Leu Lys Arg Glu Ala Val Arg
20 25 30

His Phe Pro Arg Pro Trp Leu His Gly Leu Gly Gln His Ile Tyr Glu
35 40 45

```
Thr Tyr Gly Asp Thr Trp Ala Gly Val Glu Ala Ile Ile Arg Ile Leu
    50                  55                  60

Gln Gln Leu Leu Phe Ile His Phe Arg Ile Gly Cys Gln His Ser Arg
65                  70                  75                  80

Ile Gly Ile Ile Gln Gln Arg Arg Ala Arg Arg Asn Gly Ala Ser Arg
                85                  90                  95

Ser


<210> SEQ ID NO 9
<211> LENGTH: 9804
<212> TYPE: DNA
<213> ORGANISM: Artificial Sequence
<220> FEATURE:
<223> OTHER INFORMATION: VB200705-1156knk

<400> SEQUENCE: 9

caactttgta tagaaaagtt gaagctttct ggctaactag agaacccatc gatggctccg     60

gtgcccgtca gtgggcagag cgcacatcgc ccacagtccc cgagaagttg gggggagggg    120

tcggcaattg aaccggtgcc tagagaaggt ggcgcggggt aaactgggaa agtgatgtcg    180

tgtactggct ccgccttttt cccgagggtg ggggagaacc gtatataagt gcagtagtcg    240

ccgtgaacgt tctttttcgc aacgggtttg ccgccagaac acaggtaagt gccgtgtgtg    300

gttcccgcgg gcctggcctc tttacgggtt atggcccttg cgtgccttga attacttcca    360

cctggctgca gtacgtgatt cttgatcccg agcttcgggt tggaagtggg tgggagagtt    420

cgaggccttg cgcttaagga gccccttcgc ctcgtgcttg agttgaggcc tggcctgggc    480

gctggggccg ccgcgtgcga atctggtggc accttcgcgc ctgtctcgct gctttcgata    540

agtctctagc catttaaaat ttttgatgac ctgctgcgac gctttttttc tggcaagata    600

gtcttgtaaa tgcgggccaa gatctgcaca ctggtatttc ggtttttggg gccgcgggcg    660

gcgacggggc ccgtgcgtcc cagcgcacat gttcggcgag gcggggcctg cgagcgcggc    720

caccgagaat cggacggggg tagtctcaag ctggccggcc tgctctggtg cctggtctcg    780

cgccgccgtg tatcgccccg ccctgggcgg caaggctggc ccggtcggca ccagttgcgt    840

gagcggaaag atggccgctt cccggccctg ctgcagggag ctcaaaatgg aggacgcggc    900

gctcgggaga gcgggcgggt gagtcaccca cacaaaggaa aagggccttt ccgtcctcag    960

ccgtcgcttc atgtgactcc acggagtacc gggcgccgtc caggcacctc gattagttct   1020

cgagcttttg gagtacgtcg tctttaggtt ggggggaggg gttttatgcg atggagtttc   1080

cccacactga gtgggtggag actgaagtta ggccagcttg gcacttgatg taattctcct   1140

tggaatttgc cctttttgag tttggatctt ggttcattct caagcctcag acagtggttc   1200

aaagtttttt tcttccattt caggtgtcgt gagccaccat gggtgcgcgt gcgtctggtt   1260

ctaaatctgg ctccggctct gactctggta gcaaaatcga agagctgttc aagaaacaca   1320

agatcgttgc cgtgctgcgt gccaatagtg tggaagaagc gaaaaagaaa gcgctggcgg   1380

ttttcctggg cggcgttcat ctgattgaaa ttacctttac cgtgccggat gcggataccg   1440

tgattaagga actgagcttt ctgaaggaaa tgggcgcgat tattggtgcg ggcaccgtga   1500

ccagcgtgga gcagtgccgt aaagcggtgg aaagtggcgc cgaattcatt gtgagtccgc   1560

acctggacga ggaaattagc caattttgca aggagaaggg tgtgttctat atgccaggcg   1620

ttatgacccc gaccgaactg gtgaaagcca tgaaactggg ccataccatc ttaaaactgt   1680

ttccgggtga ggtggtgggt ccgcagtttg ttaaagcgat gaaaggtccg tttccgaatg   1740
```

tgaaatttgt gccaaccggc ggtgttaatc tggacaatgt gtgcgaatgg ttcaaagcgg 1800
gcgtgctggc cgtgggcgtg ggcagcgcgt tagtgaaagg caccccggtg gaagtggcgg 1860
aaaaggccaa ggcgttcgtt gagaagattc gtggctgcac cgaacagaaa ctgattagcg 1920
aagaagatct gcagtctcgt ccggaaccga ccgcaccgcc ggaagaatct ttccgttctg 1980
gtgttgaaac caccacgcca ccgcaaaaac aggagccgat cgacaaagaa ctgtacccgc 2040
tgacctctct gcgttctctg ttcggtaacg acccgtcttc tcagtaacag acatgataag 2100
atacattgat gagtttggac aaaccacaac tagaatgcag tgaaaaaaat gctttatttg 2160
tgaaatttgt gatgctattg ctttatttgt aaccattata agctgcaata aacaagttaa 2220
caacaacaat tgcattcatt ttatgtttca ggttcagggg gaggtgtggg aggtttttta 2280
aagcaagtaa aacctctaca aatgtggtat taattaaggg ttgcgccttt tccaaggcag 2340
ccctgggttt gcgcagggac gcggctgctc tgggcgtggt tccgggaaac gcagcggcgc 2400
cgaccctggg tctcgcacat tcttcacgtc cgttcgcagc gtcacccgga tcttcgccgc 2460
taccettgtg ggcccccegg cgacgcttcc tgctccgccc ctaagtcggg aaggttcctt 2520
gcggttcgcg gcgtgccgga cgtgacaaac ggaagccgca cgtctcacta gtaccctcgc 2580
agacggacag cgccagggag caatggcagc gcgccgaccg cgatgggctg tggccaatag 2640
cggctgctca gcagggcgcg ccgagagcag cggccgggaa ggggcggtgc gggaggcggg 2700
gtgtggggcg gtagtgtggg ccctgttcct gcccgcgcgg tgttccgcat tctgcaagcc 2760
tccggagcgc acgtcggcag tcggctccct cgttgaccga atcaccgacc tctctcccca 2820
gggcctggag acgccatcca cgctgttttg acctccatag aagacaccgg gaccgatcca 2880
gcctccggtc gaccgatcct gagaacttca ggggtgagtt tggggaccct tgattgttct 2940
ttctttttcg ctattgtaaa attcatgtta tatggagggg gcaaagtttt cagggtgttg 3000
tttagaatgg gaagatgtcc cttgtatcac catggaccct catgataatt ttgtttcttt 3060
cactttctac tctgttgaca accattgtct cctcttattt tcttttcatt ttctgtaact 3120
ttttcgttaa actttagctt gcatttgtaa cgaattttta aattcacttt tgtttatttg 3180
tcagattgta agtactttct ctaatcactt ttttttcaag gcaatcaggg tatattatat 3240
tgtacttcag cacagtttta gagaacaatt gttataatta aatgataagg tagaatattt 3300
ctgcatataa attctggctg gcgtggaaat attcttattg gtagaaacaa ctacaccctg 3360
gtcatcatcc tgcctttctc tttatggtta caatgatata cactgtttga gatgaggata 3420
aaatactctg agtccaaacc gggcccctct gctaaccatg ttcatgcctt cttctctttc 3480
ctacagctcc tgggcaacgt gctggttgtt gtgctgtctc atcattttgg caaagaattc 3540
ctcgacggat ccctcgagga attctgacac tgccaccatg aagtgccttt tgtacttagc 3600
ctttttattc attggggtga attgcaagtt caccatagtt tttccacaca accaaaaagg 3660
aaactggaaa aatgttcctt ctaattacca ttattgcccg tcaagctcag atttaaattg 3720
gcataatgac ttaataggca cagccttaca agtcaaaatg cccaagagtc acaaggctat 3780
tcaagcagac ggttggatgt gtcatgcttc caaatgggtc actacttgtg atttccgctg 3840
gtatggaccg aagtatataa cacattccat ccgatccttc actccatctg tagaacaatg 3900
caaggaaagc attgaacaaa cgaaacaagg aacttggctg aatccaggct tccctcctca 3960
aagttgtgga tatgcaactg tgacggatgc cgaagcagtg attgtccagg tgactcctca 4020
ccatgtgctg gttgatgaat acacaggaga atgggttgat tcacagttca tcaacggaaa 4080

```
atgcagcaat tacatatgcc ccactgtcca taactctaca acctggcatt ctgactataa   4140
ggtcaaaggg ctatgtgatt ctaacctcat ttccatggac atcaccttct tctcagagga   4200
cggagagcta tcatccctgg gaaaggaggg cacagggttc agaagtaact actttgctta   4260
tgaaactgga ggcaaggcct gcaaaatgca atactgcaag cattggggag tcagactccc   4320
atcaggtgtc tggttcgaga tggctgataa ggatctcttt gctgcagcca gattccctga   4380
atgcccagaa gggtcaagta tctctgctcc atctcagacc tcagtggatg taagtctaat   4440
tcaggacgtt gagaggatct tggattattc cctctgccaa gaaacctgga gcaaaatcag   4500
agcgggtctt ccaatctctc cagtggatct cagctatctt gctcctaaaa acccaggaac   4560
cggtcctgct ttcaccataa tcaatggtac cctaaaatac tttgagacca gatacatcag   4620
agtcgatatt gctgctccaa tcctctcaag aatggtcgga atgatcagtg gaactaccac   4680
agaaagggaa ctgtgggatg actgggcacc atatgaagac gtggaaattg gacccaatgg   4740
agttctgagg accagttcag gatataagtt tcctttatac atgattggac atggtatgtt   4800
ggactccgat cttcatctta gctcaaaggc tcaggtgttc gaacatcctc acattcaaga   4860
cgctgcttcg caacttcctg atgatgagag tttatttttt ggtgatactg ggctatccaa   4920
aaatccaatc gagcttgtag aaggttggtt cagtagttgg aaaagctcta ttgcctcttt   4980
tttctttatc atagggttaa tcattggact attcttggtt ctccgagttg gtatccatct   5040
ttgcattaaa ttaaagcaca ccaagaaaag acagatttat acagacatag agatgaaccg   5100
acttggaaag taattttccc tctgccaaaa attatgggga catcatgaag ccccttgagc   5160
atctgacttc tggctaataa aggaaattta ttttcattgc aatagtgtgt tggaattttt   5220
tgtgtctctc actcggaagg acatatggga gggcaaatca tttaaaacat cagaatgagt   5280
atttggttta gagtttggca acatatgcca tatgctggct gccatgaaca aaggtggcta   5340
taaagaggtc atcagtatat gaaacagccc cctgctgtcc attccttatt ccatagaaaa   5400
gccttgactt gaggttagat tttttttata ttttgttttg tgttattttt ttctttaaca   5460
tccctaaaat tttccttaca tgttttacta gccagatttt tcctcctctc ctgactactc   5520
ccagtcatag ctgtccctct tctcttatga agatccctcg acctgcagcc cattaattaa   5580
caagtttgta caaaaaagca ggctcgttac ataacttacg gtaaatggcc cgcctggctg   5640
accgcccaac gacccccgcc cattgacgtc aatagtaacg ccaataggga ctttccattg   5700
acgtcaatgg gtggagtatt tacggtaaac tgcccacttg gcagtacatc aagtgtatca   5760
tatgccaagt acgcccccta ttgacgtcaa tgacggtaaa tggcccgcct ggcattgtgc   5820
ccagtacatg accttatggg actttcctac ttggcagtac atctacgtat tagtcatcgc   5880
tattaccatg gtcgaggtga gccccacgtt ctgcttcact ctccccatct cccccccctc   5940
cccaccccca attttgtatt tatttatttt ttaattattt tgtgcagcga tgggggcggg   6000
gggggggggg ggcgcgcgcc caggcggggc ggggcggggc gaggggcggg gcggggcgag   6060
gcggagaggt gcggcggcag ccaatcagag cggcgcgctc cgaaagtttc cttttatggc   6120
gaggcggcgg cggcggcggc cctataaaaa gcgaagcgcg cggcgggcgg gagtcgctgc   6180
gcgctgcctt cgccccgtgc cccgctccgc cgccgcctcg cgccgcccgc cccggctctg   6240
actgaccgcg ttactcccac aggtgagcgg gcgggacggc ccttctcctc cgggctgtaa   6300
ttagctgagc aagaggtaag ggtttaaggg atggttggtt ggtggggtat taatgtttaa   6360
ttacctggag cacctgcctg aaatcacttt ttttcaggtt ggacccagct ttcttgtaca   6420
aagtggtcta gagccaccat ggaacagaaa ctgattagcg aagaagatct ggtgagcaag   6480
```

ggcgaggagc tgttcaccgg ggtggtgccc atcctggtcg agctggacgg cgacgtaaac 6540
ggccacaagt tcagcgtgtc cggcgagggc gagggcgatg ccacctacgg caagctgacc 6600
ctgaagttca tctgcaccac cggcaagctg cccgtgccct ggcccaccct cgtgaccacc 6660
ctgacctacg gcgtgcagtg cttcagccgc taccccgacc acatgaagca gcacgacttc 6720
ttcaagtccg ccatgcccga aggctacgtc caggagcgca ccatcttctt caaggacgac 6780
ggcaactaca agacccgcgc cgaggtgaag ttcgagggcg acaccctggt gaaccgcatc 6840
gagctgaagg gcatcgactt caaggaggac ggcaacatcc tggggcacaa gctggagtac 6900
aactacaaca gccacaacgt ctatatcatg gccgacaagc agaagaacgg catcaaggtg 6960
aacttcaaga tccgccacaa catcgaggac ggcagcgtgc agctcgccga ccactaccag 7020
cagaacaccc ccatcggcga cggccccgtg ctgctgcccg acaaccacta cctgagcacc 7080
cagtccgccc tgagcaaaga ccccaacgag aagcgcgatc acatggtcct gctggagttc 7140
gtgaccgccg ccgggatcac tctcggcatg gacgagctgt acaagtctag actcgaggat 7200
atcggaggtg gcggtggagg tgaacaggca ccggaagatc aggggcctca gcgtgaaccg 7260
cataatgaat ggaccctgga actgctggaa gaactgaaac gtgaagcggt gcgtcatttc 7320
ccgcgtccgt ggctgcatgg cctgggccag catatctatg aaacctatgg cgatacctgg 7380
gctggcgtgg aagcgattat tcgtattctg cagcagctgt tgtttattca ttttcggata 7440
ggctgccaac atagccggat tggcattatt cagcagcgtc gtgcgcgtcg taatggcgcg 7500
agccgtagct aacaacttta ttatacatag ttgatggccg gccgcttcga gcagacatga 7560
taagatacat tgatgagttt ggacaaacca caactagaat gcagtgaaaa aaatgcttta 7620
tttgtgaaat ttgtgatgct attgctttat ttgtaaccat tataagctgc aataaacaag 7680
ttaacaacaa caattgcatt cattttatgt ttcaggttca gggggaggtg tgggaggttt 7740
tttaaagcaa gtaaaacctc tacaaatgtg gtagcggccg cggcgctctt ccgcttcctc 7800
gctcactgac tcgctgcgct cggtcgttcg gctgcggcga gcggtatcag ctcactcaaa 7860
ggcggtaata cggttatcca cagaatcagg ggataacgca ggaaagaaca tgtgagcaaa 7920
aggccagcaa aaggccagga accgtaaaaa ggccgcgttg ctggcgtttt tccataggct 7980
ccgcccccct gacgagcatc acaaaaatcg acgctcaagt cagaggtggc gaaacccgac 8040
aggactataa agataccagg cgtttccccc tggaagctcc ctcgtgcgct ctcctgttcc 8100
gaccctgccg cttaccggat acctgtccgc ctttctctct tcgggaagcg tggcgctttc 8160
tcatagctca cgctgtaggt atctcagttc ggtgtaggtc gttcgctcca agctgggctg 8220
tgtgcacgaa ccccccgttc agcccgaccg ctgcgcctta tccggtaact atcgtcttga 8280
gtccaacccg gtaagacacg acttatcgcc actggcagca gccactggta acaggattag 8340
cagagcgagg tatgtaggcg gtgctacaga gttcttgaag tggtggccta actacggcta 8400
cactagaaga acagtatttg gtatctgcgc tctgctgaag ccagttacct tcggaaaaag 8460
agttggtagc tcttgatccg gcaaacaaac caccgctggt agcggtggtt tttttgtttg 8520
caagcagcag attacgcgca gaaaaaaagg atctcaagaa gatcctttga tcttttctac 8580
ggggtctgac gctcagtgga acgaaaactc acgttaaggg attttggtca tgagattatc 8640
aaaaaggatc ttcacctaga tccttttaaa ttaaaaatga agttttaaat caatctaaag 8700
tatatatgag taaacttggt ctgacagtta ccaatgctta atcagtgagg cacctatctc 8760
agcgatctgt ctatttcgtt catccatagt tgcctgactc cccgtcgtgt agataactac 8820

```
gatacgggag ggcttaccat ctggccccag tgctgcaatg ataccgcgag acccacgctc   8880

accggctcca gatttatcag caataaacca gccagccgga agggccgagc gcagaagtgg   8940

tcctgcaact ttatccgcct ccatccagtc tattaattgt tgccgggaag ctagagtaag   9000

tagttcgcca gttaatagtt tgcgcaacgt tgttgccatt gctacaggca tcgtggtgtc   9060

acgctcgtcg tttggtatgg cttcattcag ctccggttcc caacgatcaa ggcgagttac   9120

atgatccccc atgttgtgca aaaaagcggt tagctccttc ggtcctccga tcgttgtcag   9180

aagtaagttg gccgcagtgt tatcactcat ggttatggca gcactgcata attctcttac   9240

tgtcatgcca tccgtaagat gcttttctgt gactggtgag tactcaacca agtcattctg   9300

agaatagtgt atgcggcgac cgagttgctc ttgcccggcg tcaatacggg ataataccgc   9360

gccacatagc agaactttaa aagtgctcat cattggaaaa cgttcttcgg ggcgaaaact   9420

ctcaaggatc ttaccgctgt tgagatccag ttcgatgtaa cccactcgtg cacccaactg   9480

atcttcagca tcttttactt tcaccagcgt ttctgggtga gcaaaaacag gaaggcaaaa   9540

tgccgcaaaa aagggaataa gggcgacacg gaaatgttga atactcatac tcttcctttt   9600

tcaatattat tgaagcattt atcagggtta ttgtctcatg agcggataca tatttgaatg   9660

tatttagaaa aataaacaaa taggggttcc gcgcacattt ccccgaaaag tgccacctga   9720

cgtctaagaa accattatta tcatgacatt aacctataaa aataggcgta tcacgaggcc   9780

ctttcgtcgg cgcgccgcgg ccgc                                          9804
```

<210> SEQ ID NO 10
<211> LENGTH: 28
<212> TYPE: DNA
<213> ORGANISM: Artificial Sequence
<220> FEATURE:
<223> OTHER INFORMATION: EcoR1-Myc-EGFP_F

<400> SEQUENCE: 10

```
gcgaattctt aattaatcta gacatgga                                        28
```

<210> SEQ ID NO 11
<211> LENGTH: 28
<212> TYPE: DNA
<213> ORGANISM: Artificial Sequence
<220> FEATURE:
<223> OTHER INFORMATION: EF1A-EcoR1_R

<400> SEQUENCE: 11

```
gcgaattcag cctgcttttt tgtacaaa                                        28
```

<210> SEQ ID NO 12
<211> LENGTH: 62
<212> TYPE: DNA
<213> ORGANISM: Artificial Sequence
<220> FEATURE:
<223> OTHER INFORMATION: VLP-Flag-Ago2_F

<400> SEQUENCE: 12

```
ttaattaatc tagacatgga ttacaaagac gatgacgata agatgtactc gggagccggc     60

cc                                                                    62
```

<210> SEQ ID NO 13
<211> LENGTH: 35
<212> TYPE: DNA
<213> ORGANISM: Artificial Sequence
<220> FEATURE:
<223> OTHER INFORMATION: VLP-Ago2_R

<400> SEQUENCE: 13
atcctcgagt ctagaagcaa agtacatggt gcgca 35

<210> SEQ ID NO 14
<211> LENGTH: 41
<212> TYPE: DNA
<213> ORGANISM: Artificial Sequence
<220> FEATURE:
<223> OTHER INFORMATION: p-delta-EGFP_Flag_F

<400> SEQUENCE: 14
gtcagatccg ctagcgccac catggattac aaagacgatg a 41

<210> SEQ ID NO 15
<211> LENGTH: 35
<212> TYPE: DNA
<213> ORGANISM: Artificial Sequence
<220> FEATURE:
<223> OTHER INFORMATION: pRP_p-delta-EGFP-C2_R

<400> SEQUENCE: 15
cagaattcga agctttttgt acaagaaagc tgggt 35

<210> SEQ ID NO 16
<211> LENGTH: 65
<212> TYPE: DNA
<213> ORGANISM: Artificial Sequence
<220> FEATURE:
<223> OTHER INFORMATION: pdEGFP_Flag-Ago2_Paz-PIWI_F

<400> SEQUENCE: 16
gtcagatccg ctagcgccac catggattac aaagacgatg acgatgcaca gccagtaatc 60
gagtt 65

<210> SEQ ID NO 17
<211> LENGTH: 65
<212> TYPE: DNA
<213> ORGANISM: Artificial Sequence
<220> FEATURE:
<223> OTHER INFORMATION: pdEGFP_Flag-Ago2_L2-PIWI_F

<400> SEQUENCE: 17
gtcagatccg ctagcgccac catggattac aaagacgatg acgatgcagg acaaagatgt 60
attaa 65

<210> SEQ ID NO 18
<211> LENGTH: 35
<212> TYPE: DNA
<213> ORGANISM: Artificial Sequence
<220> FEATURE:
<223> OTHER INFORMATION: pdEGFP_Flag-Ago2-dN-PAZ_F

<400> SEQUENCE: 18
tccgatatcc tcgagagcaa agtacatggt gcgca 35

<210> SEQ ID NO 19
<211> LENGTH: 80
<212> TYPE: DNA
<213> ORGANISM: Artificial Sequence
<220> FEATURE:
<223> OTHER INFORMATION: Ago2-Xba-Vpr_R

<400> SEQUENCE: 19
cgtacctgtc agcacgctgt tgaccttagc ccgtggcaac gactgtgaag cctccgacac 60
gtactgaggg cgattcccag 80

<210> SEQ ID NO 20
<211> LENGTH: 28
<212> TYPE: DNA
<213> ORGANISM: Artificial Sequence
<220> FEATURE:
<223> OTHER INFORMATION: kpn1-SV40_F

<400> SEQUENCE: 20
gcggtaccac ccagctttct tgtacaaa 28

<210> SEQ ID NO 21
<211> LENGTH: 31
<212> TYPE: DNA
<213> ORGANISM: Artificial Sequence
<220> FEATURE:
<223> OTHER INFORMATION: EPN01-kpn1_R

<400> SEQUENCE: 21
gcggtacctt actgagaaga cgggtcgtta c 31

<210> SEQ ID NO 22
<211> LENGTH: 35
<212> TYPE: DNA
<213> ORGANISM: Artificial Sequence
<220> FEATURE:
<223> OTHER INFORMATION: p-delta-EGFP_EPN01_F

<400> SEQUENCE: 22
gtcagatccg ctagcgccac catgggtgcg cgtgc 35

<210> SEQ ID NO 23
<211> LENGTH: 976
<212> TYPE: PRT
<213> ORGANISM: Artificial Sequence
<220> FEATURE:
<223> OTHER INFORMATION: Flag-Ago2-FL-Vpr

<400> SEQUENCE: 23

Met Asp Tyr Lys Asp Asp Asp Asp Lys Met Tyr Ser Gly Ala Gly Pro
1 5 10 15

Ala Leu Ala Pro Pro Ala Pro Pro Pro Pro Ile Gln Gly Tyr Ala Phe
20 25 30

Lys Pro Pro Pro Arg Pro Asp Phe Gly Thr Ser Gly Arg Thr Ile Lys
35 40 45

Leu Gln Ala Asn Phe Phe Glu Met Asp Ile Pro Lys Ile Asp Ile Tyr
50 55 60

His Tyr Glu Leu Asp Ile Lys Pro Glu Lys Cys Pro Arg Arg Val Asn
65 70 75 80

Arg Glu Ile Val Glu His Met Val Gln His Phe Lys Thr Gln Ile Phe
85 90 95

Gly Asp Arg Lys Pro Val Phe Asp Gly Arg Lys Asn Leu Tyr Thr Ala
100 105 110

Met Pro Leu Pro Ile Gly Arg Asp Lys Val Glu Leu Glu Val Thr Leu
115 120 125

Pro Gly Glu Gly Lys Asp Arg Ile Phe Lys Val Ser Ile Lys Trp Val
130 135 140

Ser Cys Val Ser Leu Gln Ala Leu His Asp Ala Leu Ser Gly Arg Leu
145 150 155 160

-continued

```
Pro Ser Val Pro Phe Glu Thr Ile Gln Ala Leu Asp Val Val Met Arg
                165                 170                 175

His Leu Pro Ser Met Arg Tyr Thr Pro Val Gly Arg Ser Phe Phe Thr
            180                 185                 190

Ala Ser Glu Gly Cys Ser Asn Pro Leu Gly Gly Gly Arg Glu Val Trp
        195                 200                 205

Phe Gly Phe His Gln Ser Val Arg Pro Ser Leu Trp Lys Met Met Leu
    210                 215                 220

Asn Ile Asp Val Ser Ala Thr Ala Phe Tyr Lys Ala Gln Pro Val Ile
225                 230                 235                 240

Glu Phe Val Cys Glu Val Leu Asp Phe Lys Ser Ile Glu Glu Gln Gln
                245                 250                 255

Lys Pro Leu Thr Asp Ser Gln Arg Val Lys Phe Thr Lys Glu Ile Lys
            260                 265                 270

Gly Leu Lys Val Glu Ile Thr His Cys Gly Gln Met Lys Arg Lys Tyr
        275                 280                 285

Arg Val Cys Asn Val Thr Arg Arg Pro Ala Ser His Gln Thr Phe Pro
    290                 295                 300

Leu Gln Gln Glu Ser Gly Gln Thr Val Glu Cys Thr Val Ala Gln Tyr
305                 310                 315                 320

Phe Lys Asp Arg His Lys Leu Val Leu Arg Tyr Pro His Leu Pro Cys
                325                 330                 335

Leu Gln Val Gly Gln Glu Gln Lys His Thr Tyr Leu Pro Leu Glu Val
            340                 345                 350

Cys Asn Ile Val Ala Gly Gln Arg Cys Ile Lys Lys Leu Thr Asp Asn
        355                 360                 365

Gln Thr Ser Thr Met Ile Arg Ala Thr Ala Arg Ser Ala Pro Asp Arg
    370                 375                 380

Gln Glu Glu Ile Ser Lys Leu Met Arg Ser Ala Ser Phe Asn Thr Asp
385                 390                 395                 400

Pro Tyr Val Arg Glu Phe Gly Ile Met Val Lys Asp Glu Met Thr Asp
                405                 410                 415

Val Thr Gly Arg Val Leu Gln Pro Pro Ser Ile Leu Tyr Gly Gly Arg
            420                 425                 430

Asn Lys Ala Ile Ala Thr Pro Val Gln Gly Val Trp Asp Met Arg Asn
        435                 440                 445

Lys Gln Phe His Thr Gly Ile Glu Ile Lys Val Trp Ala Ile Ala Cys
    450                 455                 460

Phe Ala Pro Gln Arg Gln Cys Thr Glu Val His Leu Lys Ser Phe Thr
465                 470                 475                 480

Glu Gln Leu Arg Lys Ile Ser Arg Asp Ala Gly Met Pro Ile Gln Gly
                485                 490                 495

Gln Pro Cys Phe Cys Lys Tyr Ala Gln Gly Ala Asp Ser Val Glu Pro
            500                 505                 510

Met Phe Arg His Leu Lys Asn Thr Tyr Ala Gly Leu Gln Leu Val Val
        515                 520                 525

Val Ile Leu Pro Gly Lys Thr Pro Val Tyr Ala Glu Val Lys Arg Val
    530                 535                 540

Gly Asp Thr Val Leu Gly Met Ala Thr Gln Cys Val Gln Met Lys Asn
545                 550                 555                 560

Val Gln Arg Thr Thr Pro Gln Thr Leu Ser Asn Leu Cys Leu Lys Ile
                565                 570                 575
```

```
Asn Val Lys Leu Gly Gly Val Asn Asn Ile Leu Leu Pro Gln Gly Arg
            580                 585                 590

Pro Pro Val Phe Gln Gln Pro Val Ile Phe Leu Gly Ala Asp Val Thr
        595                 600                 605

His Pro Pro Ala Gly Asp Gly Lys Lys Pro Ser Ile Ala Ala Val Val
    610                 615                 620

Gly Ser Met Asp Ala His Pro Asn Arg Tyr Cys Ala Thr Val Arg Val
625                 630                 635                 640

Gln Gln His Arg Gln Glu Ile Ile Gln Asp Leu Ala Ala Met Val Arg
                645                 650                 655

Glu Leu Leu Ile Gln Phe Tyr Lys Ser Thr Arg Phe Lys Pro Thr Arg
            660                 665                 670

Ile Ile Phe Tyr Arg Asp Gly Val Ser Glu Gly Gln Phe Gln Gln Val
        675                 680                 685

Leu His His Glu Leu Leu Ala Ile Arg Glu Ala Cys Ile Lys Leu Glu
    690                 695                 700

Lys Asp Tyr Gln Pro Gly Ile Thr Phe Ile Val Val Gln Lys Arg His
705                 710                 715                 720

His Thr Arg Leu Phe Cys Thr Asp Lys Asn Glu Arg Val Gly Lys Ser
                725                 730                 735

Gly Asn Ile Pro Ala Gly Thr Thr Val Asp Thr Lys Ile Thr His Pro
            740                 745                 750

Thr Glu Phe Asp Phe Tyr Leu Cys Ser His Ala Gly Ile Gln Gly Thr
        755                 760                 765

Ser Arg Pro Ser His Tyr His Val Leu Trp Asp Asp Asn Arg Phe Ser
    770                 775                 780

Ser Asp Glu Leu Gln Ile Leu Thr Tyr Gln Leu Cys His Thr Tyr Val
785                 790                 795                 800

Arg Cys Thr Arg Ser Val Ser Ile Pro Ala Pro Ala Tyr Tyr Ala His
                805                 810                 815

Leu Val Ala Phe Arg Ala Arg Tyr His Leu Val Asp Lys Glu His Asp
            820                 825                 830

Ser Ala Glu Gly Ser His Thr Ser Gly Gln Ser Asn Gly Arg Asp His
        835                 840                 845

Gln Ala Leu Ala Lys Ala Val Gln Val His Gln Asp Thr Leu Arg Thr
    850                 855                 860

Met Tyr Phe Ala Ser Arg Leu Glu Asp Ile Gly Gly Gly Gly Gly Gly
865                 870                 875                 880

Glu Gln Ala Pro Glu Asp Gln Gly Pro Gln Arg Glu Pro His Asn Glu
                885                 890                 895

Trp Thr Leu Glu Leu Leu Glu Glu Leu Lys Arg Glu Ala Val Arg His
            900                 905                 910

Phe Pro Arg Pro Trp Leu His Gly Leu Gly Gln His Ile Tyr Glu Thr
        915                 920                 925

Tyr Gly Asp Thr Trp Ala Gly Val Glu Ala Ile Ile Arg Ile Leu Gln
    930                 935                 940

Gln Leu Leu Phe Ile His Phe Arg Ile Gly Cys Gln His Ser Arg Ile
945                 950                 955                 960

Gly Ile Ile Gln Gln Arg Arg Ala Arg Arg Asn Gly Ala Ser Arg Ser
                965                 970                 975
```

<210> SEQ ID NO 24
<211> LENGTH: 750
<212> TYPE: PRT

```
<213> ORGANISM: Artificial Sequence
<220> FEATURE:
<223> OTHER INFORMATION: Flag-PAZ-PIWI-Vpr

<400> SEQUENCE: 24

Met Asp Tyr Lys Asp Asp Asp Asp Lys Ala Gln Pro Val Ile Glu Phe
1               5                   10                  15

Val Cys Glu Val Leu Asp Phe Lys Ser Ile Glu Glu Gln Gln Lys Pro
            20                  25                  30

Leu Thr Asp Ser Gln Arg Val Lys Phe Thr Lys Glu Ile Lys Gly Leu
        35                  40                  45

Lys Val Glu Ile Thr His Cys Gly Gln Met Lys Arg Lys Tyr Arg Val
    50                  55                  60

Cys Asn Val Thr Arg Arg Pro Ala Ser His Gln Thr Phe Pro Leu Gln
65                  70                  75                  80

Gln Glu Ser Gly Gln Thr Val Glu Cys Thr Val Ala Gln Tyr Phe Lys
                85                  90                  95

Asp Arg His Lys Leu Val Leu Arg Tyr Pro His Leu Pro Cys Leu Gln
            100                 105                 110

Val Gly Gln Glu Gln Lys His Thr Tyr Leu Pro Leu Glu Val Cys Asn
        115                 120                 125

Ile Val Ala Gly Gln Arg Cys Ile Lys Lys Leu Thr Asp Asn Gln Thr
    130                 135                 140

Ser Thr Met Ile Arg Ala Thr Ala Arg Ser Ala Pro Asp Arg Gln Glu
145                 150                 155                 160

Glu Ile Ser Lys Leu Met Arg Ser Ala Ser Phe Asn Thr Asp Pro Tyr
                165                 170                 175

Val Arg Glu Phe Gly Ile Met Val Lys Asp Glu Met Thr Asp Val Thr
            180                 185                 190

Gly Arg Val Leu Gln Pro Pro Ser Ile Leu Tyr Gly Gly Arg Asn Lys
        195                 200                 205

Ala Ile Ala Thr Pro Val Gln Gly Val Trp Asp Met Arg Asn Lys Gln
    210                 215                 220

Phe His Thr Gly Ile Glu Ile Lys Val Trp Ala Ile Ala Cys Phe Ala
225                 230                 235                 240

Pro Gln Arg Gln Cys Thr Glu Val His Leu Lys Ser Phe Thr Glu Gln
                245                 250                 255

Leu Arg Lys Ile Ser Arg Asp Ala Gly Met Pro Ile Gln Gly Gln Pro
            260                 265                 270

Cys Phe Cys Lys Tyr Ala Gln Gly Ala Asp Ser Val Glu Pro Met Phe
        275                 280                 285

Arg His Leu Lys Asn Thr Tyr Ala Gly Leu Gln Leu Val Val Val Ile
    290                 295                 300

Leu Pro Gly Lys Thr Pro Val Tyr Ala Glu Val Lys Arg Val Gly Asp
305                 310                 315                 320

Thr Val Leu Gly Met Ala Thr Gln Cys Val Gln Met Lys Asn Val Gln
                325                 330                 335

Arg Thr Thr Pro Gln Thr Leu Ser Asn Leu Cys Leu Lys Ile Asn Val
            340                 345                 350

Lys Leu Gly Gly Val Asn Asn Ile Leu Leu Pro Gln Gly Arg Pro Pro
        355                 360                 365

Val Phe Gln Gln Pro Val Ile Phe Leu Gly Ala Asp Val Thr His Pro
    370                 375                 380

Pro Ala Gly Asp Gly Lys Lys Pro Ser Ile Ala Ala Val Val Gly Ser
```

385 390 395 400

Met Asp Ala His Pro Asn Arg Tyr Cys Ala Thr Val Arg Val Gln Gln
405 410 415

His Arg Gln Glu Ile Ile Gln Asp Leu Ala Ala Met Val Arg Glu Leu
420 425 430

Leu Ile Gln Phe Tyr Lys Ser Thr Arg Phe Lys Pro Thr Arg Ile Ile
435 440 445

Phe Tyr Arg Asp Gly Val Ser Glu Gly Gln Phe Gln Gln Val Leu His
450 455 460

His Glu Leu Leu Ala Ile Arg Glu Ala Cys Ile Lys Leu Glu Lys Asp
465 470 475 480

Tyr Gln Pro Gly Ile Thr Phe Ile Val Val Gln Lys Arg His His Thr
485 490 495

Arg Leu Phe Cys Thr Asp Lys Asn Glu Arg Val Gly Lys Ser Gly Asn
500 505 510

Ile Pro Ala Gly Thr Thr Val Asp Thr Lys Ile Thr His Pro Thr Glu
515 520 525

Phe Asp Phe Tyr Leu Cys Ser His Ala Gly Ile Gln Gly Thr Ser Arg
530 535 540

Pro Ser His Tyr His Val Leu Trp Asp Asp Asn Arg Phe Ser Ser Asp
545 550 555 560

Glu Leu Gln Ile Leu Thr Tyr Gln Leu Cys His Thr Tyr Val Arg Cys
565 570 575

Thr Arg Ser Val Ser Ile Pro Ala Pro Ala Tyr Tyr Ala His Leu Val
580 585 590

Ala Phe Arg Ala Arg Tyr His Leu Val Asp Lys Glu His Asp Ser Ala
595 600 605

Glu Gly Ser His Thr Ser Gly Gln Ser Asn Gly Arg Asp His Gln Ala
610 615 620

Leu Ala Lys Ala Val Gln Val His Gln Asp Thr Leu Arg Thr Met Tyr
625 630 635 640

Phe Ala Ser Arg Leu Glu Asp Ile Gly Gly Gly Gly Gly Gly Glu Gln
645 650 655

Ala Pro Glu Asp Gln Gly Pro Gln Arg Glu Pro His Asn Glu Trp Thr
660 665 670

Leu Glu Leu Leu Glu Glu Leu Lys Arg Glu Ala Val Arg His Phe Pro
675 680 685

Arg Pro Trp Leu His Gly Leu Gly Gln His Ile Tyr Glu Thr Tyr Gly
690 695 700

Asp Thr Trp Ala Gly Val Glu Ala Ile Ile Arg Ile Leu Gln Gln Leu
705 710 715 720

Leu Phe Ile His Phe Arg Ile Gly Cys Gln His Ser Arg Ile Gly Ile
725 730 735

Ile Gln Gln Arg Arg Ala Arg Arg Asn Gly Ala Ser Arg Ser
740 745 750

<210> SEQ ID NO 25
<211> LENGTH: 629
<212> TYPE: PRT
<213> ORGANISM: Artificial Sequence
<220> FEATURE:
<223> OTHER INFORMATION: Flag-L2-PIWI-Vpr

<400> SEQUENCE: 25

Met Asp Tyr Lys Asp Asp Asp Asp Lys Ala Gly Gln Arg Cys Ile Lys

```
1               5                   10                  15

Lys Leu Thr Asp Asn Gln Thr Ser Thr Met Ile Arg Ala Thr Ala Arg
            20                  25                  30

Ser Ala Pro Asp Arg Gln Glu Glu Ile Ser Lys Leu Met Arg Ser Ala
        35                  40                  45

Ser Phe Asn Thr Asp Pro Tyr Val Arg Glu Phe Gly Ile Met Val Lys
    50                  55                  60

Asp Glu Met Thr Asp Val Thr Gly Arg Val Leu Gln Pro Pro Ser Ile
65                  70                  75                  80

Leu Tyr Gly Gly Arg Asn Lys Ala Ile Ala Thr Pro Val Gln Gly Val
                85                  90                  95

Trp Asp Met Arg Asn Lys Gln Phe His Thr Gly Ile Glu Ile Lys Val
            100                 105                 110

Trp Ala Ile Ala Cys Phe Ala Pro Gln Arg Gln Cys Thr Glu Val His
        115                 120                 125

Leu Lys Ser Phe Thr Glu Gln Leu Arg Lys Ile Ser Arg Asp Ala Gly
    130                 135                 140

Met Pro Ile Gln Gly Gln Pro Cys Phe Cys Lys Tyr Ala Gln Gly Ala
145                 150                 155                 160

Asp Ser Val Glu Pro Met Phe Arg His Leu Lys Asn Thr Tyr Ala Gly
                165                 170                 175

Leu Gln Leu Val Val Val Ile Leu Pro Gly Lys Thr Pro Val Tyr Ala
            180                 185                 190

Glu Val Lys Arg Val Gly Asp Thr Val Leu Gly Met Ala Thr Gln Cys
        195                 200                 205

Val Gln Met Lys Asn Val Gln Arg Thr Thr Pro Gln Thr Leu Ser Asn
    210                 215                 220

Leu Cys Leu Lys Ile Asn Val Lys Leu Gly Gly Val Asn Asn Ile Leu
225                 230                 235                 240

Leu Pro Gln Gly Arg Pro Pro Val Phe Gln Gln Pro Val Ile Phe Leu
                245                 250                 255

Gly Ala Asp Val Thr His Pro Pro Ala Gly Asp Gly Lys Lys Pro Ser
            260                 265                 270

Ile Ala Ala Val Val Gly Ser Met Asp Ala His Pro Asn Arg Tyr Cys
        275                 280                 285

Ala Thr Val Arg Val Gln Gln His Arg Gln Glu Ile Ile Gln Asp Leu
    290                 295                 300

Ala Ala Met Val Arg Glu Leu Leu Ile Gln Phe Tyr Lys Ser Thr Arg
305                 310                 315                 320

Phe Lys Pro Thr Arg Ile Ile Phe Tyr Arg Asp Gly Val Ser Glu Gly
                325                 330                 335

Gln Phe Gln Gln Val Leu His His Glu Leu Leu Ala Ile Arg Glu Ala
            340                 345                 350

Cys Ile Lys Leu Glu Lys Asp Tyr Gln Pro Gly Ile Thr Phe Ile Val
        355                 360                 365

Val Gln Lys Arg His His Thr Arg Leu Phe Cys Thr Asp Lys Asn Glu
    370                 375                 380

Arg Val Gly Lys Ser Gly Asn Ile Pro Ala Gly Thr Thr Val Asp Thr
385                 390                 395                 400

Lys Ile Thr His Pro Thr Glu Phe Asp Phe Tyr Leu Cys Ser His Ala
                405                 410                 415

Gly Ile Gln Gly Thr Ser Arg Pro Ser His Tyr His Val Leu Trp Asp
            420                 425                 430
```

Asp Asn Arg Phe Ser Ser Asp Glu Leu Gln Ile Leu Thr Tyr Gln Leu
435 440 445

Cys His Thr Tyr Val Arg Cys Thr Arg Ser Val Ser Ile Pro Ala Pro
450 455 460

Ala Tyr Tyr Ala His Leu Val Ala Phe Arg Ala Arg Tyr His Leu Val
465 470 475 480

Asp Lys Glu His Asp Ser Ala Glu Gly Ser His Thr Ser Gly Gln Ser
485 490 495

Asn Gly Arg Asp His Gln Ala Leu Ala Lys Ala Val Gln Val His Gln
500 505 510

Asp Thr Leu Arg Thr Met Tyr Phe Ala Ser Arg Leu Glu Asp Ile Gly
515 520 525

Gly Gly Gly Gly Gly Glu Gln Ala Pro Glu Asp Gln Gly Pro Gln Arg
530 535 540

Glu Pro His Asn Glu Trp Thr Leu Glu Leu Leu Glu Glu Leu Lys Arg
545 550 555 560

Glu Ala Val Arg His Phe Pro Arg Pro Trp Leu His Gly Leu Gly Gln
565 570 575

His Ile Tyr Glu Thr Tyr Gly Asp Thr Trp Ala Gly Val Glu Ala Ile
580 585 590

Ile Arg Ile Leu Gln Gln Leu Leu Phe Ile His Phe Arg Ile Gly Cys
595 600 605

Gln His Ser Arg Ile Gly Ile Ile Gln Gln Arg Arg Ala Arg Arg Asn
610 615 620

Gly Ala Ser Arg Ser
625

<210> SEQ ID NO 26
<211> LENGTH: 531
<212> TYPE: PRT
<213> ORGANISM: Artificial Sequence
<220> FEATURE:
<223> OTHER INFORMATION: Flag-MID-PIWI-Vpr

<400> SEQUENCE: 26

Met Asp Tyr Lys Asp Asp Asp Asp Lys Ile Glu Ile Lys Val Trp Ala
1 5 10 15

Ile Ala Cys Phe Ala Pro Gln Arg Gln Cys Thr Glu Val His Leu Lys
20 25 30

Ser Phe Thr Glu Gln Leu Arg Lys Ile Ser Arg Asp Ala Gly Met Pro
35 40 45

Ile Gln Gly Gln Pro Cys Phe Cys Lys Tyr Ala Gln Gly Ala Asp Ser
50 55 60

Val Glu Pro Met Phe Arg His Leu Lys Asn Thr Tyr Ala Gly Leu Gln
65 70 75 80

Leu Val Val Val Ile Leu Pro Gly Lys Thr Pro Val Tyr Ala Glu Val
85 90 95

Lys Arg Val Gly Asp Thr Val Leu Gly Met Ala Thr Gln Cys Val Gln
100 105 110

Met Lys Asn Val Gln Arg Thr Thr Pro Gln Thr Leu Ser Asn Leu Cys
115 120 125

Leu Lys Ile Asn Val Lys Leu Gly Gly Val Asn Asn Ile Leu Leu Pro
130 135 140

Gln Gly Arg Pro Pro Val Phe Gln Gln Pro Val Ile Phe Leu Gly Ala
145 150 155 160

-continued

```
Asp Val Thr His Pro Pro Ala Gly Asp Gly Lys Lys Pro Ser Ile Ala
                165                 170                 175

Ala Val Val Gly Ser Met Asp Ala His Pro Asn Arg Tyr Cys Ala Thr
            180                 185                 190

Val Arg Val Gln Gln His Arg Gln Glu Ile Ile Gln Asp Leu Ala Ala
        195                 200                 205

Met Val Arg Glu Leu Leu Ile Gln Phe Tyr Lys Ser Thr Arg Phe Lys
    210                 215                 220

Pro Thr Arg Ile Ile Phe Tyr Arg Asp Gly Val Ser Glu Gly Gln Phe
225                 230                 235                 240

Gln Gln Val Leu His His Glu Leu Leu Ala Ile Arg Glu Ala Cys Ile
                245                 250                 255

Lys Leu Glu Lys Asp Tyr Gln Pro Gly Ile Thr Phe Ile Val Val Gln
            260                 265                 270

Lys Arg His His Thr Arg Leu Phe Cys Thr Asp Lys Asn Glu Arg Val
        275                 280                 285

Gly Lys Ser Gly Asn Ile Pro Ala Gly Thr Thr Val Asp Thr Lys Ile
    290                 295                 300

Thr His Pro Thr Glu Phe Asp Phe Tyr Leu Cys Ser His Ala Gly Ile
305                 310                 315                 320

Gln Gly Thr Ser Arg Pro Ser His Tyr His Val Leu Trp Asp Asp Asn
                325                 330                 335

Arg Phe Ser Ser Asp Glu Leu Gln Ile Leu Thr Tyr Gln Leu Cys His
            340                 345                 350

Thr Tyr Val Arg Cys Thr Arg Ser Val Ser Ile Pro Ala Pro Ala Tyr
        355                 360                 365

Tyr Ala His Leu Val Ala Phe Arg Ala Arg Tyr His Leu Val Asp Lys
    370                 375                 380

Glu His Asp Ser Ala Glu Gly Ser His Thr Ser Gly Gln Ser Asn Gly
385                 390                 395                 400

Arg Asp His Gln Ala Leu Ala Lys Ala Val Gln Val His Gln Asp Thr
                405                 410                 415

Leu Arg Thr Met Tyr Phe Ala Ser Arg Leu Glu Asp Ile Gly Gly Gly
            420                 425                 430

Gly Gly Gly Glu Gln Ala Pro Glu Asp Gln Gly Pro Gln Arg Glu Pro
        435                 440                 445

His Asn Glu Trp Thr Leu Glu Leu Leu Glu Glu Leu Lys Arg Glu Ala
    450                 455                 460

Val Arg His Phe Pro Arg Pro Trp Leu His Gly Leu Gly Gln His Ile
465                 470                 475                 480

Tyr Glu Thr Tyr Gly Asp Thr Trp Ala Gly Val Glu Ala Ile Ile Arg
                485                 490                 495

Ile Leu Gln Gln Leu Leu Phe Ile His Phe Arg Ile Gly Cys Gln His
            500                 505                 510

Ser Arg Ile Gly Ile Ile Gln Gln Arg Arg Ala Arg Arg Asn Gly Ala
        515                 520                 525

Ser Arg Ser
    530
```